(12) United States Patent
Varadarajan et al.

(10) Patent No.: US 10,344,058 B2
(45) Date of Patent: Jul. 9, 2019

(54) POLYPEPTIDES FOR GENERATING ANTI-INFLUENZA ANTIBODIES AND USES THEREOF

(71) Applicant: INDIAN INSTITUTE OF SCIENCE, Bangalore (IN)

(72) Inventors: Raghavan Varadarajan, Bangalore (IN); Vamsee V. Aditya Mallajosyula, Bangalore (IN)

(73) Assignee: INDIAN INSTITUTE OF SCIENCE, Bangalore (IN)

( * ) Notice: Subject to any disclaimer, the term of this patent is extended or adjusted under 35 U.S.C. 154(b) by 11 days.

(21) Appl. No.: 15/305,575

(22) PCT Filed: Apr. 29, 2015

(86) PCT No.: PCT/IB2015/000589
§ 371 (c)(1),
(2) Date: Oct. 20, 2016

(87) PCT Pub. No.: WO2015/166329
PCT Pub. Date: Nov. 5, 2015

(65) Prior Publication Data
US 2017/0204142 A1 Jul. 20, 2017

(30) Foreign Application Priority Data
May 1, 2014 (IN) .......................... 2208/CHE/2014

(51) Int. Cl.
C07K 14/005 (2006.01)
A61K 39/145 (2006.01)

(52) U.S. Cl.
CPC .......... *C07K 14/005* (2013.01); *A61K 39/145* (2013.01); *C07K 2319/40* (2013.01); *C12N 2760/16034* (2013.01); *C12N 2760/16134* (2013.01)

(58) Field of Classification Search
None
See application file for complete search history.

(56) References Cited

FOREIGN PATENT DOCUMENTS

| WO | 2010117786 A1 | 10/2010 |
| WO | 2013079473 A1 | 6/2013 |
| WO | 2013177444 A2 | 11/2013 |

OTHER PUBLICATIONS

PDB: 4NCW_B (2014) (Year: 2014).*
International Search Report and Written Opinion for PCT App No. PCT/IB2015/000589 dated Jul. 17, 2015, 14 pgs.
(Continued)

*Primary Examiner* — Michelle S Horning
(74) *Attorney, Agent, or Firm* — Procopio, Cory, Hargreaves & Savitch LLP

(57) ABSTRACT

The present disclosure relates to a polypeptide comprising hemagglutinin stem domain fragments that can elicit broadly cross-reactive anti-influenza antibodies and confer protection against influenza virus. The disclosure also provides a method of preparing the polypeptide with biochemical and biophysical properties that enhance its immunogenic properties. Also provided are recombinant DNA constructs, vectors, and host cells comprising the nucleic acid encoding the polypeptide, as well as uses of the polypeptide, particularly in the prevention, and detection of influenza.

Figure 1:
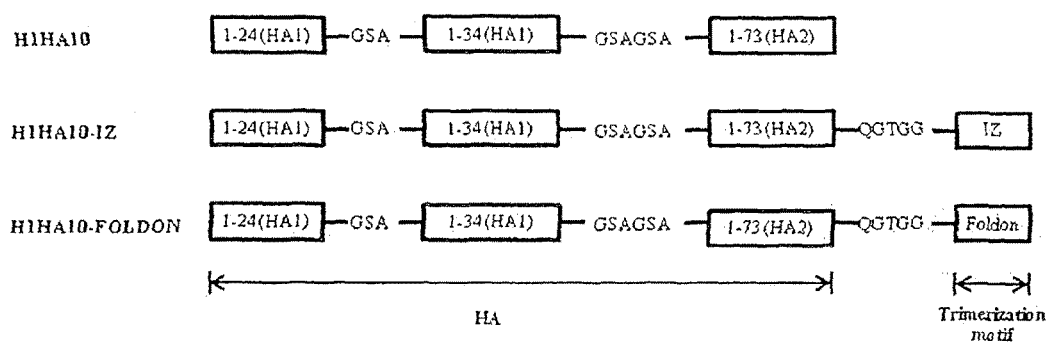

24 Claims, 9 Drawing Sheets
Specification includes a Sequence Listing.

(56) References Cited

OTHER PUBLICATIONS

Bommakanti, G., et al., Design of *Escherichia coli*-Expressed Stalk Domain Immunogens of H1N1 Hemagglutinin That Protect Mice from Lethal Challenge, Journal of Virology, 86(24), Sep. 26, 2012, pp. 13434-13444.
Lu, Y., et al., Production and Stabilization of the Trimeric Influenza Hemagglutinin Stem Domain for Potentially Broadly Protective Influenza Vaccines, Proc Natl Acad Sci USA, 111(1), Jan. 7, 2014, pp. 125-130.
Mallajosyula, V.V.A., et al., Influenza Hemagglutinin Stem-Fragment Immunogen Elicits Broadly Neutralizing Antibodies and Confers Heterologous Protection, 111(25), Jun. 24, 2014, pp. E2514-E2523.
Steel, J., et al., Influenza Virus Vaccine Based on the Conserved Hemagglutinin Stalk Domain, mBIO, American Society for Microbiology, 1(1), May 18, 2010, 9 pgs.
Bhattacharyya, S., et al., Design of an *Escherichia coli* Expressed HIV-1 gp120 Fragment Immunogen that Binds to b12 and Induces Broad and Potent Neutralizing Antibodies, The Journal of Biological Chemistry, 288(14), Apr. 5, 2013, pp. 9815-9825.
Bommakanti, G., et al., Design of an HA2-based *Escherichia coli* Expressed Influenza Immunogen that Protects Mice from Pathogenic Challenge, PNAS, 107(31), Aug. 3, 2010, pp. 13701-13706.
Bommakanti, G., et al., Design of *Escherichia coli*-Expressed Stalk Domain Immunogens of H1N1 Hemagglutinin that Protect Mice from Lethal Challenge, Journal of Virology, 86(24), Dec. 2012, pp. 13434-13444.
Carr, C. M., et al., A Spring-Loaded Mechanism for the Conformational Change of Influenza Hemagglutinin, Cell 73, May 21, 1993, pp. 823-832.
Carrat, F., et al., Influenza Vaccine: The Challenge of Antigenic Drift, Vaccine, 25, 2007, pp. 6852-6862.
Chen, J., et al., A Soluble Domain of the Membrane-Anchoring Chain of the Influenza Virus Hemmagglutinin (HA2) Folds in *Escherichia coli* into the Low-pH-Induced Confirmation, Proc. Natl. Acad. Sci., 92, Dec. 1995, pp. 12205-12209.
Copeland, C. S., et al., Assembly of Influenza Hemagglutinin Trimers and its Role in Intracellular Transport, The Journal of Cell Biology, 103, Oct. 1986, pp. 1179-1191.
Corti, D., et al., A Neutralizing Antibody Selected from Plasma Cells that Binds to Group 1 and Group 2 Influenza A Hemagglutinins, Science, 333, 2011, pp. 850-856.
Ekiert, D. C., et al., Antibody Recognition of a Highly Conserved Influenza Virus Epitope, Science, 324, Apr. 10, 2009, pp. 246-251.
Ekiert, D. C., et al., Cross-Neutralization of Influenza A Viruses Mediated by a Single Antibody Loop, Nature, 489, Sep. 27, 2012, pp. 526-532.
Ellebedy, A. H., et al., Re-Engaging Cross-Reactive Memory B Cells: The Influenza Puzzle, Frontiers in Immunology, 3(53), Mar. 30, 2012, 7 pgs.
Gamblin, S. J., The Structure and Receptor Binding Properties of the 1918 Influenza Hemagglutinin, Science, 303, Mar. 19, 2004, pp. 1838-1842.
Ganesh, C., et al., Thermodynamic Characterization of the Reversible Two-State Unfolding of Maltose Binding Protein, a Large Two-Domain Protein, Biochemistry, 36, 1997, pp. 5020-5028.
Guthe, S., et al., Very Fast Folding and Association of a Trimerization Domain from Bacteriophage T4 Fibritin, J. Mol. Biol., 337, 2004, pp. 905-915.
Harris, A. K., et al., Structure and Accessibility of HA Trimers on Intact 2009 H1N1 Pandemic Influenza Virus to Stem Region-Specific Neutralizing Antibodies, PNAS, 110(12), Mar. 19, 2013, pp. 4592-4597.
Higgins, D. G., et al., Clustal: A Package for Performing Multiple Sequence Alignment on a Microcomputer, Gene, 73, 1988, pp. 237-244.

Hong, M., et al., Antibody Recognition of the Pandemic H1N1 Influenza Virus Hemagglutinin Receptor Binding Site, Journal of Virology, 87(22), Nov. 2013, pp. 12471-12480.
Huang, Y., et al., CD-HIT Suite: A Web Server for Clustering and Comparing Biological Sequences, Bioinformatics, 26(5), 2010, pp. 680-682.
Hwang, T-L., et al., Water Suppression that Works. Excitation Sculpting Using Arbitrary Waveforms and Pulsed Field Gradients, Journal of Magnetic Resonance, Series A 112, 1995, pp. 275-279.
Julien, J-P, et al., Structural Insights into Key Sites of Vulnerability on HIV-1 Env and Influenza HA, Immunological Reviews, 250, 2012, pp. 180-198.
Knossow, M., et al., Variation and Infectivity Neutralization in Influenza, Immunology, 119, 2006, pp. 1-7.
Krause, J. C., et al., A Broadly Neutralizing Human Monoclonal Antibody that Recognizes a Conserved, Novel Epitope on the Globular Head of the Influenza H1N1 Virus Hemagglutinin, Journal of Virology, 85(20), Oct. 2011, pp. 10905-10908.
Kwong, P. D., et al., HIV-1 and Influenza Antibodies: Seeing Antigens in New Ways, Nature Immunology, 10(6), Jun. 2009, pp. 573-578.
Lee, P. S., Heterosubtypic Antibody Recognition of the Influenza Virus Hemagglutinin Receptor Binding Site Enhanced by Avidity, PNAS, 109(42), Oct. 16, 2012, pp. 17040-17045.
Lu, Y., et al., Production and Stabilization of the Trimeric Influenza Hemagglutinin Stem Domain for Potentially Broadly Protective Influenza Vaccines, PNAS, 111(1), Jan. 7, 2014, pp. 125-130.
Mallajosyula, V. A., et al., Influenza Hemagglutinin Stem-Fragment Immunogen Elicits Broadly Neutralizing Antibodies and Confers Heterologous Protection, PNAS, 111(25), Jun. 24, 2014, pp. E2514-E2523.
Ohshima, N., et al., Naturally Occuring Antibodies in Humans Can Neutralize a Variety of Influenza Virus Strain, Including H3, H1, H2, and H5, Journal of Virology, 85(21), Nov. 2011, pp. 11048-11057.
Okuno, Y., et al., Protection Against the Mouse-Adapted A/FM/1/47 Strain of Influenza A Virus in Mice by aMonoclonal Antibody with Cross-Neutralizing Activity Among H1 and H2 Strains, Journal of Virology, 68(1), Jan. 1994, pp. 157-520.
Pica, N., et al., Towards a Universal Influenza Virus Vaccine: Prospects and Challenges, Annu. Rev. Med., 64, 2013, pp. 189-202.
Saha, P., et al., Design and Characterization of Stabilized Derivatives of Human CD4D12 and CD4D1, Biochemistry, 50, 2011, pp. 7891-7900.
Schmidt, A. G., et al., Preconfiguration of the Antigen-Binding Site Dureing Affinity Maturation of the Broadly Neutralizing Influenza Virus Antibody, PNAS, 110(1), Jan. 2, 2013, pp. 264-269.
Sharma, D., et al., Protein Minimization of the gp120 Binding Region of Human CD4, Biochemistry, 44, 2005, pp. 16192-16202.
Shembekar, N., et al., Isolation of a High Affinity Neutralizing Monoclonal Antibody Against 2009 Pandemic H1N1 Virus that Binds at the 'Sa' Antigenic Site, PLoS One, 8(1), Jan. 2013, 10 pgs.
Skehel, J. J., et al., Receptor Binding and Membrane Fusion in Virus Entry: The Influenza Hemagglutinin, Annu. Rev. Biochem., 69, 2000, pp. 531-569.
Song, L., et al., Efficacious Recombinant Influenza Vaccines Produced by High Yield Bacterial Expression: A Solution to Global Pandemic and Seasonal Needs, PLoS One, 3(5), May 2008, 8 pgs.
Steel, J., et al., Influenza Virus Vaccine Based on the Conserved Hemagglutinin Stalk Domain, MBio, 1(1), Apr. 2010, 9 pgs.
Stevens, J., et al., Structure and Receptor Specificity of the Hemagglutinin from an H5N1 Influenza Virus, Science, 312, Apr. 21, 2006, pp. 404-410.
Sui, J. et al., Structural and Functional Bases for Broad-Spectrum Neutralization of Avian and Human Influenza A Viruses, Nature Structural & Molecular Biology, 16(3), Mar. 2009, pp. 265-273.
Suzuki, K., et al., An Isoleucine Zipper Peptide Forms a Native-Like Triple Stranded Coiled Coil in Solution, Protein Engineering, 11(11), 1998, pp. 1051-1055.
Tong, S., et al., New World Bats Harbor Diverse Influenza A Viruses, PLoS One, 9(10), Oct. 2013, 12 pgs.

(56) References Cited

OTHER PUBLICATIONS

Tsibane, T., et al., Influenza Human Monoclonal Antibody 1F1 Interacts with Three Major Antigenic Sites and Residues Mediating Human Receptor Specificity in H1N1 Viruses, PLoS One, 8(12), Dec. 2012, 9 pgs.

Varadarajan, R., et al., Characterization of gp120 and Its Single-Chain Derivatives, gp120-CD4D12 and gp120-M9: Implications for Targeting the CD4i Epitope in Human Immunodeficiency Virus Vaccine Design, Journal of Virology, 79(3), pp. 1713-1723.

Whittle, J. R. R., et al., Broadly Neutralizing Human Antibody that Recognizes the Receptor-Binding Pocket of Influenza Virus Hemagglutinin, PNAS, 108(34), Aug. 23, 2011, pp. 14216-14221.

Wrammert, J., et al., Broadly Cross-Reactive Antibodies Dominate the Human B Cell Response Against 2009 Pandemic H1N1 Influenza Virus Infection, J Exp Med, 208(1), Jan. 17, 2011, pp. 181-193.

Xu, R., et al., A Recurring Motif for Antibody Recognition of the Receptor-Binding Site of Influenza Hemagglutinin, Nature Structural & Molecular Biology, 20(3), Mar. 2013, pp. 363-370.

Valkenburg, S.A., et al., Stalking Influenza by Vaccination with Pre-Fusion Headless HA Mini-Stem, Scientific Reports, 6, Article No. 22666, 2016, 11 pgs.

\* cited by examiner

POLYPEPTIDES FOR GENERATING ANTI-INFLUENZA ANTIBODIES AND USES THEREOF

CROSS-REFERENCE TO RELATED APPLICATIONS

This application is a U.S. National Stage entry of PCT Application No. PCT/IB2015/000589, filed on Apr. 29, 2015, which claims priority to IN Application No. 2208/CHE/2014 filed May 1, 2014. The contents of the foregoing are incorporated by reference.

FIELD OF INVENTION

The present disclosure relates to the field of molecular biology, virology, and immunology. In particular, the present disclosure relates to polypeptides comprising two influenza HA1 stem fragments, and one HA2 fragment that elicit neutralizing antibodies against influenza virus. The present disclosure also provides a method for making the polypeptide, and uses thereof.

BACKGROUND OF THE INVENTION

Seasonal influenza outbreaks across the globe cause an estimated 250,000 to 500,000 deaths annually. Current influenza vaccines need to be updated every few years because of antigenic drift (Pica el al., *Annu Rev Med.,* 2013, 64,189-202). Despite intensive monitoring, strain mismatch between vaccine formulation and influenza viruses circulating within the population has occurred in the past (Carrat et al., *Vaccine,* 2007, 25(39-40), 6852-6862). Public health is further compromised when an unpredictable mixing event among influenza virus genomes leads to antigenic shift facilitating a potential pandemic outbreak. These concerns have expedited efforts towards developing a 'universal' flu vaccine.

Neutralizing antibodies (nAbs) against hemagglutinin (HA) are the primary correlate for protection in humans and hence HA is an attractive target for vaccine development (Gerhard, *Curr Top Microbiol Immunol.,* 2001, 260,171-190). The precursor polypeptide, HA0, is assembled into a trimer along the secretory pathway and transported to the cell surface. Cleavage of HA0 generates the disulfide linked HA1 and HA2 subunits. Mature HA has a globular head domain which mediates receptor binding and is primarily composed of the HA1. subunit while the stem domain predominantly comprises of the HA2 subunit. The HA stem is trapped in a metastable state and undergoes an extensive low-pH induced conformational rearrangement in the host-cell endosomes to adopt the virus-host membrane fusion competent state (Carr et al., *Cell,* 1993, 73(4), 823-832; Skehel et al., *Annu Rev Biochem.,* 2000, 69, 531-569).

The antigenic sites on the globular head of HA are subjected to heightened immune pressure resulting in escape variants; thereby limiting the breadth of head-directed nAbs (Knossow et al., *Immunology,* 2006, 119(1), 1-7). However, extensive efforts have resulted in the isolation of monoclonal antibodies which bind within the globular head and inhibit receptor attachment, which neutralize drifted variants of an HA subtype or heterosubtypic HA subtype (Ekiert D C, et al.,*Nature,* 2012, 489(7417), 526-532; Hong M, et al. *J Virol.,* 2013, 87(22), 12471-12480; Krause J C, et al., *J Virol.,* 2011, 85(20), 10905-10908; Lee P S, et al., *Proc Natl Acad Sci USA,* 2012, 109(42), 17040-17045; Ohshima N, et al., *J Virol.,* 2011, 85(21), 11048-11057; Schmidt A G, et al., *Proc Natl Acad Sci USA,* 2013, 110(1), 264-269; Tsibane T, et al., *PLoS Pathog,* 2012, 8(12), e1003067; Whittle J R, et al., *Proc Natl Acad Sci USA,* 2011, 108(34), 14216-14221; Wrammert J, et al., *J Exp Med.,* 2011, 208(1), 181-193; Xu R, et al., *Nat Struct Mol Biol.,* 2013, 20(3), 363-370).

The HA stem is targeted by several neutralizing antibodies (bnAbs) with neutralizing activity against diverse influenza A virus subtypes (Julien J P et al., *Immunol Rev.,* 2012, 250(1), 180-198). The epitopes of these bnAbs in the HA stem are more conserved across different influenza HA subtypes compared to the antigenic sites in the HA globular head (Ellebedy A H et al., *Front Immunol.,* 2012, 3, 53).

A 'headless' stem domain immunogen offers an attractive solution. However, early attempts at expressing the HA2-subunit independently in a native, pre-fusion conformation have been unsuccessful. In the absence of the head domain, the HA2-subunit expressed in *E. coli* spontaneously adopts a low-pH conformation (Chen J, et al., *Proc Natl Acad Sci USA,* 1995, 92(26), 12205-12209) in which the functional epitopes of stem-directed bnAbs are disrupted. More recently, the entire HA stem region has been expressed in a pre-fusion, native-like conformation in both prokaryotic and eukaryotic systems adopting multiple strategies (Bommakanti G, et al., *Proc Natl Acad Sci USA,* 2010, 107(31), 13701-1370; Bommakanti G, et al., *J Virol,* 2012, 86(24), 13434-13444; Lu Y et al., *Proc Natl Acad Sci USA,* 2014, 111(1), 125-130; Steel J, et al., *M Bio.,* 2010, 1(1)).

U.S. Pat. No. 6,720,409 provides an anti-human influenza virus antibody which recognizes the stem regions of haemagglutinin molecules of the H1N1 and H2N2 subtypes and has a neutralization activity but does not recognize the stem region of the H3N2 subtype and has no neutralization activity.

WO2013011347 describes antibodies, and antigen binding fragments thereof, that specifically bind to an epitope in the stem region of an influenza A hemagglutinin trimer and neutralize a group I subtype and a group 2 subtype of influenza A virus.

U.S. Pat. No. 5,589,174describes an anti-human influenza virus antibody is provided having the following characteristics: (a) specifically binds to the stem region of hemagglutinin of human influenza A virus subtype H3N2; (b) does not specifically bind to the stem region of hemagglutinin of human influenza A virus subtypes H1N1 and H2N2; and (c) does not specifically bind to the stem region of hemagglutinin of human influenza B virus.

WO201377444 describes vaccine compositions and methods of producing and using the same, which compositions comprise a modified HA stem domain in trimeric configuration.

SUMMARY OF THE INVENTION

An aspect of the present disclosure relates to a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

An aspect of the present disclosure relates to a recombinant DNA construct comprising a polynucleotide fragment operably linked to a promoter, wherein said polynucleotide fragment encodes a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

An aspect of the present disclosure relates to a recombinant vector comprising a recombinant DNA construct comprising a polynucleotide fragment operably linked to a promoter, wherein said polynucleotide fragment encodes a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

An aspect of the present disclosure relates to a recombinant host cell comprising a recombinant vector comprising a recombinant DNA construct comprising a polynucleotide fragment operably linked to a promoter, wherein said polynucleotide fragment encodes a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker, wherein the recombinant host cell is selected from the group consisting of a bacterial cell, fungal cell, and mammalian cell, preferably *E. coli*.

An aspect of the present disclosure relates to an influenza vaccine comprising a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

An aspect of the present disclosure relates to a method to produce a vaccine against influenza, said method comprising: (a) expressing a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker, in a host cell, and (b) purifying the expressed polypeptide from step (a).

An aspect of the present disclosure relates to a method to vaccinate an individual against influenza, said method comprising administering a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker, to an individual such that said polypeptide elicits an immune response against influenza virus.

An aspect of the present disclosure relates to a method of detection of influenza virus in a host, said method comprising: (a) obtaining a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker, (b) contacting serum from a host with the polypeptide from step (a), and (c) carrying out an ELISA test, wherein formation and detection of antibody and polypeptide complexes is indicative of presence of influenza virus in said host.

An aspect of the present disclosure relates to an influenza vaccine comprising a polynucleotide fragment encoding a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

An aspect of the present disclosure relates to an influenza vaccine comprising a polypeptide, said polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

In an aspect of the present disclosure, there is provided a use of a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, wherein the amino acid sequence of the third subunit shares atleast 70%-100% sequence similarity to an amino acid sequence as set forth in SEQ ID NO: 3, and wherein each subunit is connected by a linker as a vaccine against influenza.

In an aspect of the present disclosure, there is provided a method of administering a vaccine to a subject in need of creating an immune response against influenza in said subject cell tissue, said method comprising of: a) obtaining a therapeutically or prophylactically effective amount of an influenza vaccine comprising a polynucleotide fragment encoding a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker; or an influenza vaccine comprising said polypeptide; or said polypeptide; and b) administering said effective amount of influenza vaccine or polypeptide to said subject, wherein said method creates an immune response against influenza.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

FIG. 1 depicts the fragments of the HA stem used in construct of the polypeptide connected by flexible, soluble linkers, and derivatives with C-terminal trimerization motif, in accordance with an embodiment of the present disclosure.

FIG. 2 depicts the spectra of the polypeptides as determined by CD-spectroscopy, in accordance with an embodiment of the present disclosure.

FIG. 3 depicts the NMR spectra of H1HA10-Foldon, in accordance with an embodiment of the present disclosure.

FIG. 4 depicts the oligomeric state of polypeptides, in accordance with an embodiment of the present disclosure.

FIG. 5 depicts the limited proteolysis resistance of polypeptides, in accordance with an embodiment of the present disclosure.

FIG. 6A-F depicts the breadth of the antibody response elicited by the polypeptides as determined by ELISA, in accordance with an embodiment of the present disclosure.

FIG. 7 depicts the binding competition of polypeptides with the bnAb CR6261, in accordance with an embodiment of the present disclosure.

FIG. 8A-B depicts the protection effected by polypeptide in mice against lethal homologous challenge, in accordance with an embodiment of the present disclosure.

FIG. 9 depicts the subtype specific and limited cross group protection afforded in-vivo by polypeptides, in accordance with an embodiment of the present disclosure.

FIG. 10A-B depicts the thermal stability of polypeptides, in accordance with an embodiment of the present disclosure.

FIG. 11A-C depicts the fluorescence emission spectra of polypeptides, in accordance with an embodiment of the present disclosure.

FIG. 12A-D depicts the binding kinetics of polypeptides at different concentrations, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The term "bnAbs/bnAb" refers to broad neutralizing antibodies.

The term "nAbs/nAb" refers to neutralizing antibodies.

The term "IZ" refers to isoleucine zipper.

H1HA10 refers to a polypeptide having amino acid sequence as set forth in SEQ ID NO: 35, encoded by a nucleotide sequence as set forth in SEQ ID NO: 41.

H1HA10-IZ refers to a polypeptide having amino acid sequence as set forth in SEQ ID NO: 36, encoded by a nucleotide sequence as set forth in SEQ ID NO: 42.

H1HA1-Foldon refers to a polypeptide having amino acid sequence as set forth in SEQ ID NO: 37, encoded by a nucleotide sequence as set forth in SEQ ID NO: 43.

NCH1HA10-Foldon refers to a polypeptide having amino acid sequence as set forth in SEQ ID NO: 38, encoded by a nucleotide sequence as set forth in SEQ ID NO: 44.

pH1HA10-Foldon refers to a polypeptide having amino acid sequence as set forth in SEQ ID NO: 39, encoded by a nucleotide sequence as set forth in SEQ ID NO: 45.

H5HA10-Foldon refers to a polypeptide having amino acid sequence as set forth in SEQ ID NO: 40, encoded by a nucleotide sequence as set forth in SEQ ID NO: 46.

The term "immunogen/test immunogen" refers to the polypeptide as described herein and the terms immunogen or polypeptide may be used interchangeably.

Sequence Description

SEQ ID NO: 1 depict the amino acid sequence of H1N1 A/Puerto Rico/8/34 HA1 stem fragment.

SEQ ID NO: 2 depict the amino acid sequence of H1N1 A/Puerto Rico/8/34 HA1 stem fragment.

SEQ ID NO: 3 depict the amino acid sequence of H1N1 A/Puerto Rico/8/34 HA2 stem fragment.

SEQ ID NO: 4 depict the nucleotide sequence encoding a polypeptide having amino acid sequence as set forth in SEQ ID NO: 1.

SEQ ID NO: 5 depict the nucleotide sequence encoding a polypeptide having amino acid sequence as set forth in SEQ ID NO: 2.

SEQ ID NO: 6 depict the nucleotide sequence encoding a polypeptide having amino acid sequence as set forth in SEQ ID NO: 3.

SEQ ID NO: 7 depict the amino acid sequence of H1N1 A/Puerto Rico/8/34 or H1N1 A/New Caledonia/20/99HA1 stem fragment.

SEQ ID NO: 8 depict the amino acid sequence of H1N1 A/California/04/2009 HA1 stem fragment.

SEQ ID NO: 9 depict the amino acid sequence of H5N1 A/Viet Nam/1203/2004 HA1 stem fragment.

SEQ ID NO: 10 depict the modified amino acid sequence of H1N1 A/Puerto Rico/8/34 HA1 stem fragment.

SEQ ID NO: 11 depict the modified amino acid sequence of H1N1 A/New Caledonia/20/99HA1 stem fragment.

SEQ ID NO: 12 depict the modified amino acid sequence of H1N1 A/California/04/2009 HA1 stem fragment.

SEQ ID NO: 13 depict the modified amino acid sequence of H5N1 A/Viet Nam/1203/2004 HA1 stem fragment.

SEQ ID NO: 14 depict the modified amino acid sequence of H1N1 A/Puerto Rico/8/34 HA2 stem fragment.

SEQ ID NO: 15 depict the modified amino acid sequence of H1N1 A/New Caledonia/20/99 HA2 stem fragment.

SEQ ID NO: 16 depict the modified amino acid sequence of H1N1 A/California/04/2009 HA2 stem fragment.

SEQ ID NO: 17 depict the modified amino acid sequence of H5N1 A/Viet Nam/1203/2004 HA2 stem fragment.

SEQ ID NO: 18 depict the nucleotide sequence encoding a polypeptide having amino acid sequence as set forth in SEQ ID NO: 7.

SEQ ID NO: 19 depict the nucleotide sequence encoding a polypeptide having amino acid sequence as set forth in SEQ ID NO: 8.

SEQ ID NO: 20 depict the nucleotide sequence encoding a polypeptide having amino acid sequence as set forth in SEQ ID NO: 9.

SEQ ID NO: 21 depict the nucleotide sequence encoding a polypeptide having amino acid sequence as set forth in SEQ ID NO: 10.

SEQ ID NO: 22 depict the nucleotide sequence encoding a polypeptide having amino acid sequence as set forth in SEQ ID NO: 11.

SEQ ID NO: 23 depict the nucleotide sequence encoding a polypeptide having amino acid sequence as set forth in SEQ ID NO: 12.

SEQ ID NO: 24 depict the nucleotide sequence encoding a polypeptide having amino acid sequence as set forth in SEQ ID NO: 13.

SEQ ID NO: 25 depict the nucleotide sequence encoding a polypeptide having amino acid sequence as set forth in SEQ ID NO: 14.

SEQ ID NO: 26 depict the nucleotide sequence encoding a polypeptide having amino acid sequence as set forth in SEQ ID NO: 15.

SEQ ID NO: 27 depict the nucleotide sequence encoding a polypeptide having amino acid sequence as set forth in SEQ ID NO: 16.

SEQ ID NO: 28 depict the nucleotide sequence encoding a polypeptide having amino acid sequence as set forth in SEQ ID NO: 17.

SEQ ID NO: 29 depict the nucleotide sequence encoding a linker peptide having amino acid sequence as set forth in SEQ ID NO: 30.

SEQ ID NO: 30 depict the amino acid sequence of linker.

SEQ ID NO: 31 depict the isoleucine-zipper (IZ) amino acid sequence.

SEQ ID NO: 32 depict the Foldon amino acid acid sequence.

SEQ ID NO: 33 depict the nucleotide sequence encoding a polypeptide having amino acid sequence as set forth in SEQ ID NO: 31.

SEQ ID NO: 34 depict the nucleotide sequence encoding a polypeptide having amino acid sequence as set forth in SEQ ID NO: 32.

SEQ ID NO: 35 depict the amino acid sequence of H1HA10 (H1N1 A/Puerto Rico/8/34).

SEQ ID NO: 36 depict the amino acid sequence of H1HA1-IZ.

SEQ ID NO: 37 depict the amino acid sequence of H1HA1-Foldon.

SEQ ID NO: 38 depict the amino acid sequence of NCH1HA1-Foldon (H1N1 A/New Caledonia/20/99).

SEQ ID NO: 39 depict the amino acid sequence of pH1HA1-Foldon (H1N1 A/California/04/2009).

SEQ ID NO: 40 depict the amino acid sequence of H5HA10-Foldon (H5N1 A/Viet Nam/1203/2004).

SEQ ID NO: 41 depict the nucleotide sequence encoding a polypeptide having amino acid sequence as set forth in SEQ ID NO: 35.

SEQ ID NO: 42 depict the nucleotide sequence encoding a polypeptide having amino acid sequence as set forth in SEQ ID NO: 36.

SEQ ID NO: 43 depict the nucleotide sequence encoding a polypeptide having amino acid sequence as set forth in SEQ ID NO: 37.

SEQ ID NO: 44 depict the nucleotide sequence encoding a polypeptide having amino acid sequence as set forth in SEQ ID NO: 38.

SEQ ID NO: 45 depict the nucleotide sequence encoding a polypeptide having amino acid sequence as set forth in SEQ ID NO: 39.

SEQ ID NO: 46 depict the nucleotide sequence encoding a polypeptide having amino acid sequence as set forth in SEQ ID NO: 40.

SEQ ID NO: 47 depict the amino acid sequence of linker.

SEQ ID NO: 48 depict the nucleotide sequence encoding a linker peptide having amino acid sequence as set forth in SEQ ID NO: 47.

SEQ ID NO: 49 depict amino acid sequence of linker.

SEQ ID NO: 50 depict amino acid sequence of linker.

SEQ ID NO: 51 depict amino acid sequence of linker.

SEQ ID NO: 52 depict the nucleotide sequence encoding a linker peptide having amino acid sequence as set forth in SEQ ID NO: 49.

SEQ ID NO: 53 depict the nucleotide sequence encoding a linker peptide having amino acid sequence as set forth in SEQ ID NO: 50.

SEQ ID NO: 54 depict the nucleotide sequence encoding a linker peptide having amino acid sequence as set forth in SEQ ID NO: 51.

In an embodiment of the present disclosure, there is provided a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

In an aspect of the present disclosure, there is provided a polypeptide comprising a first subunit, a second subunit, and a third subunit connected by linkers, wherein the amino acid sequence of the first subunit shares 70%, 75%, 80%, 85%, 90%, 95%, or 100% sequence similarity to an amino acid sequence as set forth in SEQ ID NO: 1.

In a preferred embodiment of the present disclosure, the amino acid sequence of the first subunit is selected from the group consisting of SEQ ID NO: 7, SEQ ID NO: 8 and SEQ ID NO: 9.

In a preferred embodiment of the present disclosure, the nucleotide sequence encoding the first subunit is selected from the group consisting of SEQ ID NO: 18, SEQ ID NO: 19, and SEQ ID NO: 20.

In an aspect of the present disclosure, there is provided a polypeptide comprising a first subunit, a second subunit, and a third subunit connected by linkers, wherein the amino acid sequence of the second subunit shares 70%, 75%, 80%, 85%, 90%, 95%, or 100% sequence similarity to an amino acid sequence as set forth in SEQ ID NO: 2.

In a preferred embodiment of the present disclosure, the amino acid sequence of the second subunit is selected from the group consisting of SEQ ID NO: 10, SEQ ID NO: II, SEQ ID NO: 12, and SEQ ID NO: 13.

In a preferred embodiment of the present disclosure, the nucleotide sequence encoding the second subunit is selected from the group consisting of SEQ ID NO: 21, SEQ ID NO: 22, SEQ ID NO: 23, and SEQ ID NO: 24.

In an aspect of the present disclosure, there is provided a polypeptide comprising a first subunit, a second subunit, and a third subunit connected by linkers, wherein the amino acid sequence of the third subunit shares 70%, 75%, 80%, 85%, 90%, 95%, or 100% sequence similarity to an amino acid sequence as set forth in SEQ ID NO: 3.

In a preferred embodiment of the present disclosure, the amino acid sequence of the third subunit is selected from the group consisting of SEQ ID NO: 14, SEQ ID NO: 15, SEQ ID NO: 16, and SEQ ID NO: 17.

In a preferred embodiment of the present disclosure, the nucleotide sequence encoding the third subunit is selected from the group consisting of SEQ ID NO: 25, SEQ ID NO: 26, SEQ ID NO: 27, and SEQ ID NO: 28.

In as aspect of the present disclosure, there is provided a polypeptide as described herein, wherein the first, second, and third subunit is optionally modified.

In a preferred embodiment of the present disclosure, there is provided a polypeptide as described herein, wherein the first subunit is unmodified.

In a preferred embodiment of the present disclosure, there is provided a polypeptide as described herein, wherein the second subunit is modified.

In a preferred embodiment of the present disclosure, there is provided a polypeptide as described herein, wherein the third subunit is modified.

In an embodiment of the present disclosure, there is provided a polypeptide as described herein, wherein the second subunit having amino acid sequence atleast 70% similar to a sequence as set forth in SEQ ID NO: 2 is modified at amino acid residues selected from the group consisting of 19, V12, 114, and C17.

In a preferred embodiment of the present disclosure, there is provided a polypeptide as described herein, wherein the amino acid modifications in the second subunit having amino acid sequence as set forth in SEQ ID NO: 2 are 19T, V12T, 114N, and C17S.

In an embodiment of the present disclosure, there is provided a polypeptide as described herein, wherein the third subunit having amino acid sequence atleast 70% similar to a sequence as set forth in SEQ ID NO: 3 is modified at amino acid residues selected from the group consisting of V26, F70, F23, L33, S14, and N42.

In a preferred embodiment of the present disclosure, there is provided a polypeptide as described herein, wherein the amino acid modifications in the third subunit having amino acid sequence as set forth in SEQ ID NO: 3 are V26, F70A, F23D, L33D, S14T, and N42K.

In an embodiment of the present disclosure, there is provided a polypeptide as described herein, wherein the nucleotide sequence encoding the first subunit shares atleast 70%-100% sequence similarity to a polynucleotide sequence as set forth in SEQ ID NO: 4, wherein the nucleotide sequence encoding the second subunit shares atleast 70%-100% sequence similarity to a polynucleotide sequence as set forth in SEQ ID NO: 5, and wherein the nucleotide sequence encoding the third subunit shares atleast 70%-100% sequence similarity to a polynucleotide sequence as set forth in SEQ ID NO: 6.

In an embodiment of the present disclosure, there is provided a polypeptide as described herein, wherein the nucleotide sequence encoding the first subunit shares 70%, 75%, 80%, 85%, 90%, 95%, or 100% sequence similarity to a polynucleotide sequence as set forth in SEQ ID NO: 4.

In an embodiment of the present disclosure, there is provided a polypeptide as described herein, wherein the nucleotide sequence encoding the second subunit shares 70%, 75%, 80%, 85%, 90%, 95%, or 100% sequence similarity to a polynucleotide sequence as set forth in SEQ ID NO: 5.

In an embodiment of the present disclosure, there is provided a polypeptide as described herein, wherein the nucleotide sequence encoding the third subunit shares 70%, 75%, 80%, 85%, 90%, 95%, or 100% sequence similarity to a polynucleotide sequence as set forth in SEQ ID NO: 6.

In an embodiment of the present disclosure, there is provided a polypeptide as described herein, wherein the amino acid sequence of the first subunit is selected from the group consisting of SEQ ID NO: 7, SEQ ID NO: 8, and SEQ ID NO: 9.

In an embodiment of the present disclosure, there is provided a polypeptide as described herein, wherein the amino acid sequence of the second subunit is selected from the group consisting of SEQ ID NO: 10, SEQ ID NO: 11, SEQ ID NO: 12, and SEQ ID NO: 13.

In an embodiment of the present disclosure, there is provided a polypeptide as described herein, wherein the amino acid sequence of the third subunit is selected from the group consisting of SEQ ID NO: 14, SEQ ID NO: 15, SEQ ID NO: 16, and SEQ ID NO: 17.

In an embodiment of the present disclosure, there is provided a polypeptide as described herein, wherein the nucleotide sequence encoding the first subunit is selected from the group consisting of SEQ ID NO: SEQ ID NO: 18, SEQ ID NO: 19, and SEQ ID NO: 20.

In an embodiment of the present disclosure, there is provided a polypeptide as described herein, wherein the nucleotide sequence encoding the second subunit is selected from the group consisting of SEQ ID NO: 21, SEQ ID NO: 22, SEQ ID NO: 23, and SEQ ID NO: 24.

In an embodiment of the present disclosure, there is provided a polypeptide as described herein, wherein the nucleotide sequence encoding the third subunit is selected from the group consisting of SEQ ID NO: 25, SEQ ID NO: 26, SEQ ID NO: 27, and SEQ ID NO: 28.

In an embodiment of the present disclosure, there is provided a polypeptide as described herein, wherein the linker of variable length has amino acid sequence as set forth in SEQ ID NO: 30.

In an embodiment of the present disclosure, there is provided a polypeptide as described herein, wherein the nucleotide sequence encoding the linker having amino acid sequence as set forth in SEQ ID NO: 30 is as set forth in SEQ ID NO: 29.

In an embodiment of the present disclosure, there is provided a polypeptide as described herein, wherein the linker of variable length has amino acid sequence as set forth in SEQ ID NO: 49.

In an embodiment of the present disclosure, there is provided a polypeptide as described herein, wherein the nucleotide sequence encoding the linker having amino acid sequence as set forth in SEQ ID NO: 49 is as set forth in SEQ ID NO: 52.

In an embodiment of the present disclosure, there is provided a polypeptide as described herein, wherein the linker of variable length has amino acid sequence as set forth in SEQ ID NO: 50.

In an embodiment of the present disclosure, there is provided a polypeptide as described herein, wherein the nucleotide sequence encoding the linker having amino acid sequence as set forth in SEQ ID NO: 50 is as set forth in SEQ ID NO: 53.

In an embodiment of the present disclosure, there is provided a polypeptide as described herein, wherein the linker of variable length has amino acid sequence as set forth in SEQ ID NO: 51.

In an embodiment of the present disclosure, there is provided a polypeptide as described herein, wherein the nucleotide sequence encoding the linker having amino acid sequence as set forth in SEQ ID NO: 51 is as set forth in SEQ ID NO: 54.

In a preferred embodiment of the present disclosure, there is provided a polypeptide as described herein, wherein the linker of variable length has amino acid sequence as set forth in SEQ ID NO: 47.

In a preferred embodiment of the present disclosure, there is provided a polypeptide as described herein, wherein the nucleotide sequence encoding the linker having amino acid sequence as set forth in SEQ ID NO: 47 is as set forth in SEQ ID NO: 48.

In an embodiment of the present disclosure, there is provided a polypeptide as described herein, wherein the amino acid sequence of the linker of variable length is GGG.

In an embodiment of the present disclosure, there is provided a polypeptide as described herein, wherein the nucleotide sequence encoding the linker having amino acid sequence GGG is GGTGGCGGT.

In an embodiment of the present disclosure, there is provided a polypeptide as described herein, wherein the amino acid sequence of the linker of variable length is GSG.

In an embodiment of the present disclosure, there is provided a polypeptide as described herein, wherein the nucleotide sequence encoding the linker having amino acid sequence GGG is GGCTCTGGT.

In an embodiment of the present disclosure, there is provided a polypeptide as described herein, wherein the amino acid sequence of the linker of variable length is GSS.

In an embodiment of the present disclosure, there is provided a polypeptide as described herein, wherein the nucleotide sequence encoding the linker having amino acid sequence GGG is GGTTCTTCC.

In a preferred embodiment of the present disclosure, there is provided a polypeptide as described herein, wherein the amino acid sequence of the linker of variable length is GSA.

In a preferred embodiment of the present disclosure, there is provided a polypeptide as described herein, wherein the nucleotide sequence encoding the linker having amino acid sequence GSA is GGCAGCGCG.

In an embodiment of the present disclosure, the number of amino acid residues as set forth in SEQ ID NO: 30 or SEQ ID NO: 47 or SEQ ID NO 49 or SEQ ID NO: 50 or SEQ ID NO: 51 is modified to contain 1 less amino acid residue.

In an embodiment of the present disclosure, the number of amino acid residues as set forth in SEQ ID NO: 30 or SEQ ID NO: 47 or SEQ ID NO 49 or SEQ ID NO: 50 or SEQ ID NO: 51 is modified to contain 1-3 extra amino acid residues.

In an embodiment of the present disclosure, the linker having amino acid sequence selected from the group consisting of GSA, GGG, GSG, and GSS is modified to contain 1 less amino acid residue.

In an embodiment of the present disclosure, the linker having amino acid sequence selected from the group consisting of GSA, GGG, GSG, and GSS is modified to contain 1-3 extra amino acid residues.

In a preferred embodiment of the present disclosure, there is provided a polypeptide as described herein, wherein the amino acid sequence of the linkers of variable length are GSA or SEQ ID NO: 47 or as set forth in SEQ ID NO: 30.

In an embodiment of the present disclosure, the nucleotide sequence encoding the amino acid sequence of the linkers as described herein is codon optimized for host specific expression.

In a preferred embodiment of the present disclosure, there is provided a polypeptide as described herein, further comprising a C-terminal trimerization domain.

In an embodiment of the present disclosure, the amino acid sequence of the C-terminal trimerization motif is selected from the group consisting of SEQ ID NO: 31, and SEQ ID NO: 32.

In an embodiment of the present disclosure, the nucleotide sequence encoding the C-terminal trimerization motif is selected from the group consisting of SEQ ID NO: 33, and SEQ ID NO: 34.

In an embodiment of the present disclosure, there is provided a polypeptide as described herein, wherein the amino acid sequence of the polypeptide is selected from the group consisting of SEQ ID NO: 35, SEQ ID NO: 36, SEQ ID NO: 37, SEQ ID NO: 38, SEQ ID NO: 39 and SEQ ID NO: 40.

In a preferred embodiment of the present disclosure, there is provided a polypeptide comprising a C-terminal trimerization motif as described herein, wherein the amino acid sequence of the C-terminal trimerization motif is as set forth in SEQ ID NO: 32.

In an embodiment of the present disclosure, there is provided a polypeptide as described herein, wherein the nucleotide sequence encoding the polypeptide is selected from the group consisting of SEQ ID NO: 41, SEQ ID NO: 42, SEQ ID NO: 43, SEQ ID NO: 44, SEQ ID NO: 45 and SEQ ID NO: 46.

In a preferred embodiment of the present disclosure, the polypeptide as described herein is soluble.

In a preferred embodiment of the present disclosure, there polypeptide as described herein lacks disulfide bridges.

In a preferred embodiment of the present disclosure, there polypeptide as described herein lacks glycosylated amino acid residues.

In a preferred embodiment of the present disclosure, there polypeptide as described herein is thermotolerant.

In a preferred embodiment of the present disclosure, there polypeptide as described herein elicits/boosts broadly cross-reactive, anti-influenza antibodies.

In a preferred embodiment of the present disclosure, there polypeptide as described herein is folded and predominantly alpha-helical.

In a preferred embodiment of the present disclosure, there polypeptide as described herein has native, neutral pH like confirmation.

In an embodiment of the present disclosure, there is provided a recombinant DNA construct comprising a polynucleotide fragment operably linked to a promoter, wherein said polynucleotide fragment encodes a polypeptide as described herein.

In an embodiment of the present disclosure, there is provided a recombinant vector comprising a recombinant DNA construct comprising a polynucleotide fragment operably linked to a promoter, wherein said polynucleotide fragment encodes a polypeptide as described herein.

In an embodiment of the present disclosure, there is provided a recombinant host cell comprising a recombinant DNA construct comprising a polynucleotide fragment operably linked to a promoter, wherein said polynucleotide fragment encodes a polypeptide as described herein.

In a preferred embodiment of the present disclosure, there is provided a recombinant host cell comprising a recombinant vector, wherein the recombinant vector comprises a recombinant DNA construct comprising a polynucleotide fragment operably linked to a promoter, wherein said polynucleotide fragment encodes a polypeptide as described herein.

In an embodiment of the present disclosure, the recombinant host cell is a bacterial cell.

In a preferred embodiment of the present disclosure, the recombinant host cell is *E. coli.*

In an embodiment of the present disclosure, the recombinant host cell is a fungal cell.

In an embodiment of the present disclosure, the recombinant host cell is a plant cell.

In an embodiment of the present disclosure, the recombinant host cell is a mammalian cell.

In an embodiment of the present disclosure, there is provided an influenza vaccine comprising a polypeptide as described herein.

In an embodiment of the present disclosure, there is provided an influenza vaccine comprising a polynucleotide fragment encoding a polypeptide as described herein.

In an embodiment of the present disclosure, there is provided a method to produce a vaccine against influenza, said method comprising (a) expressing a polypeptide as described herein in a host cell as described herein, and (b) purifying the expressed polypeptide from step (a).

In an embodiment of the present disclosure, the polypeptide expressed by a method as described herein is present in the soluble fraction of the cell lysate.

In an embodiment of the present disclosure, the polypeptide expressed by a method as described herein is thermotolerant.

In an embodiment of the present disclosure, the polypeptide expressed by a method as described herein has native, neutral pH like confirmation.

In an embodiment of the present disclosure, the polypeptide expressed by a method as described herein elicits/boosts broadly cross-reactive, anti-influenza antibodies.

In an embodiment of the present disclosure, there is provided a method to vaccinate an individual against influenza, said method comprising administering a polypeptide as described herein to an individual such that said polypeptide elicits an immune response against influenza virus.

In an embodiment of the present disclosure, there is provided a use of a polypeptide as described herein to isolate antibodies in animals that are specific to influenza virus stem region.

In an embodiment of the present disclosure, the polypeptide used to isolate antibodies as described herein is selected from the group consisting of polypeptides having amino acid sequence as set forth in SEQ ID NO: 35, SEQ ID NO: 36, SEQ ID NO: 37, SEQ ID NO: 39, and SEQ ID NO: 40.

In an embodiment of the present disclosure, the polypeptide isolate antibodies as described herein is encoded by a nucleotide fragment having nucleotide sequence selected from the group consisting of SEQ ID NO: 41, SEQ ID NO: 42, SEQ ID NO: 43, SEQ ID NO: 44, SEQ ID NO: 45, and SEQ ID NO: 46.

In an embodiment of the present disclosure, there is provided a method of detection of influenza virus in a host, said method comprising (a) obtaining a polypeptide as described herein, (b) contacting serum from a host with the polypeptide from step (a), and (c) carrying out an ELISA test, wherein formation and detection of antibody and polypeptide complexes is indicative of presence of influenza in said host.

In an embodiment of the present disclosure, the polypeptide used in a method of detection of influenza in a host as described herein is selected from the group consisting of polypeptides having amino acid sequence as set forth in SEQ ID NO: 35, SEQ ID NO: 36, SEQ ID NO" 37, SEQ ID NO: 39, and SEQ ID NO: 40.

In an embodiment of the present disclosure, the polypeptide used in a method of detection of influenza in a host cell as described herein is encoded by a nucleotide fragment having nucleotide sequence selected from the group consisting of SEQ ID NO: 41, SEQ ID NO: 42, SEQ ID NO: 43, SEQ ID NO: 44, SEQ ID NO: 45, and SEQ ID NO: 46.

In a preferred embodiment of the present disclosure, the host is a mammal.

In an embodiment of the present disclosure, the host is a bird.

In an embodiment of the present disclosure, the host is a poultry bird.

In an embodiment of the present disclosure, none of the introduced amino acid modifications in SEQ ID NO: 2 or SEQ ID NO: 3 are in the epitopes of stem directed broad neutralizing antibodies, CR6261, F10, or F16v3 as described previously in the prior art.

In an embodiment of the present disclosure, a polypeptide lacking a C-terminal trimerization motif as described herein is predominantly present as monomeric conformer in solution.

In an embodiment of the present disclosure, a polypeptide having a C-terminal trimerization motif as described herein, wherein the amino acid sequence of the C-terminal trimerization motif is as set forth in SEQ ID NO: 31 is a mixture of stable trimeric and monomeric conformers in solution, wherein the percentage of stable trimeric conformers in said solution is in the range of 60%-70%, and the percentage of stable monomeric conformers in said solution is in the range of 30%-40%.

In an embodiment of the present disclosure, there is provided a polypeptide having a C-terminal trimerization motif having amino acid sequence as set forth in SEQ ID NO: 32, wherein atleast 90% of said polypeptide is predominantly present as trimeric conformer in solution.

In an embodiment of the present disclosure, there is provided a polypeptide having a C-terminal trimerization motif having amino acid sequence as set forth in SEQ ID NO: 32, wherein atleast 95% of said polypeptide is predominantly present as trimeric conformer in solution.

In an embodiment of the present disclosure, the polypeptide as described herein shows limited resistance to proteolysis.

In an embodiment of the present disclosure, the polypeptide as described herein binds with stem directed broad neutralizing antibody CR6261 as described previously in the prior art.

In a preferred embodiment of the present disclosure, the polypeptide as described herein binds with stem directed broad neutralizing antibody CR6261 with sub-micromolar affinity.

In an embodiment of the present disclosure, C-terminal trimerization motifs assist in folding of H1HA10.

In an embodiment of the present disclosure, the degree of proteolytic resistance is as follows: H1HA10<H1HA10-IZ<H1HA10-Foldon.

In an embodiment of the present disclosure, all polypeptides as described herein elicit higher cross reactive antibody titers compared to mice immunized with PR8 virus.

In a preferred embodiment of the present disclosure, H1HA10-Foldon elicits highest cross reactive antibody titers.

In an embodiment of the present disclosure, the polypeptides as described herein protect mice against lethal homologous challenge.

In a preferred embodiment of the present disclosure, H1HA10 provides atleast approximately 2 fold higher protection to mice against lethal homologous challenge compared to naïve group.

In a more preferred embodiment of the present disclosure, H1HA10-IZ provides atleast approximately 2 fold higher protection to mice against lethal homologous challenge compared to naïve group.

In a most preferred embodiment of the present disclosure, H1HA10-Foldon provides approximately 2 fold higher protection to mice against lethal homologous challenge compared to naïve group.

In an embodiment of the present disclosure, the polypeptides as described herein confer robust subtype specific protection in-vivo.

In an embodiment of the present disclosure, the polypeptides as described herein confer limited cross group protection in-vivo.

In an embodiment of the present disclosure, H1HA10-Foldon shows thermal stability from approximately 300K-350K.

In an embodiment of the present disclosure, the polypeptides as described herein bind the confirmation-specific influenza hemagglutinin stem directed bnAb CR6261 as described previously in the prior art.

In an embodiment of the present disclosure, the first subunit of the polypeptide as described herein comprises of amino acids 18-41 of HA1 stem of influenza virus.

In an embodiment of the present disclosure, the second subunit of the polypeptide as described herein comprises of amino acids 290-323 of HA1 stem of influenza virus.

In an embodiment of the present disclosure, the third subunit of the polypeptide as described herein comprises of amino acids 41-113 of HA2 stem of influenza virus.

In an embodiment of the present disclosure, amino acid residues of other strains of influenza virus that are homologous to the modified amino acids in the subunits of the polypeptide as described herein may be modified to yield an immunogen with biochemical or biophysical properties similar to the polypeptide as described herein.

In an embodiment of the present disclosure, the NCB1-Flu database accession number for H1N1 A/Puerto Rico 8/1934 is ABD77675.1.

In an embodiment of the present disclosure, the NCB1-Flu database accession number for H1N1 A/New Caledonia/20/1999 is ACF41878.1.

In an embodiment of the present disclosure, the NCB1-Flu database accession number for H1N1 A/California/04/2009 is ACS45305.1.

In an embodiment of the present disclosure, the NCB1-Flu database accession number for H1N1 A/Viet Nam/1203/2004 is ABW90125.1.

In an embodiment of the present disclosure, there is provided a polypeptide as described herein, wherein the first subunit has atleast 24 contiguous amino acids selected from amino acid residues 12-55 of HA1 stem of H1N1 A/Puerto Rico 8/1934.

In a preferred embodiment of the present disclosure, there is provided a polypeptide as described herein, wherein the amino acid sequence of the first subunit as set forth in SEQ ID NO: 1 shares 100% sequence homology with amino acid residues 18-41 of HA1 stem of H1N1 A/Puerto Rico 8/1934.

In an embodiment of the present disclosure, there is provided a polypeptide as described herein, wherein the second subunit has atleast 34 contiguous amino acids selected from amino acid residues 280-340 of HA1 stem of H1N1 A/Puerto Rico 8/1934.

In a preferred embodiment of the present disclosure, there is provided a polypeptide as described herein, wherein the amino acid sequence of the second subunit as set forth in SEQ ID NO: 2 shares 100% sequence homology with amino acid residues 290-323 of HA1 stem of H1N1 A/Puerto Rico 8/1934.

In an embodiment of the present disclosure, there is provided a polypeptide as described herein, wherein the third subunit has atleast 73 contiguous amino acids selected from amino acid residues 30-130 of HA2 stem of H1N1 A/Puerto Rico 8/1934.

In a preferred embodiment of the present disclosure, there is provided a polypeptide as described herein, wherein the amino acid sequence of the third subunit as set forth in SEQ ID NO: 3 shares 100% sequence homology with amino acid residues 41-113 of HA2 stem of H1N1 A/Puerto Rico 8/1934.

In an embodiment of the present disclosure, there is provided an influenza vaccine comprising polypeptide, said polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

In an embodiment of the present disclosure, there is provided an influenza vaccine comprising a polynucleotide fragment encoding a polypeptide comprising a first subunit, a second subunit, and a third subunit, wherein the amino acid sequence of the first subunit shares atleast 70%-100% sequence similarity to an amino acid sequence as set forth in SEQ ID NO: 1, wherein, the amino acid sequence of the second subunit shares atleast 70%-100% sequence similarity to an amino acid sequence as set forth in SEQ ID NO: 2, and wherein the amino acid sequence of the third subunit shares atleast 70%-100% sequence similarity to an amino acid sequence as set forth in SEQ ID NO: 3, wherein each subunit is connected by a linker.

In a preferred embodiment of the present disclosure, there is provided an influenza vaccine comprising a polynucleotide fragment as described herein, wherein the nucleotide sequence of the polynucleotide fragment is as set forth in SEQ ID NO: 35.

In an embodiment of the present disclosure, there is provided an influenza vaccine as described herein, said influenza vaccine further comprising of pharmaceutically acceptable carriers, diluents, and excipients.

In an embodiment of the present disclosure, there is provided a use of a polypeptide as described herein as a vaccine against influenza.

In an embodiment of the present disclosure, there is provided a method of administering a vaccine to a subject in need of creating an immune response against influenza in said subject cell tissue, said method comprising of: a) obtaining a therapeutically or prophylactically effective amount of an influenza vaccine as described herein; and b) administering said effective amount of influenza vaccine to said subject, wherein said method creates an immune response against influenza.

In an embodiment of the present disclosure, there is provided a method of administering a vaccine to a subject in need of creating an immune response against influenza in said subject cell tissue, said method comprising of: a) obtaining a therapeutically or prophylactically effective amount of a polypeptide as described herein; and b) administering said effective amount of polypeptide to said subject, wherein said method creates an immune response against influenza.

In an embodiment of the present disclosure, there is provided a method of administering a vaccine to a subject in need of creating an immune response against influenza in said subject cell tissue as described herein, wherein said administration is oral.

In an embodiment of the present disclosure, there is provided a method of administering a vaccine to a subject in need of creating an immune response against influenza in said subject cell tissue as described herein, wherein said administration is intramuscular.

In an embodiment of the present disclosure, there is provided a method of administering a vaccine to a subject in need of creating an immune response against influenza in said subject cell tissue as described herein, wherein said administration is intraperitoneal.

In an embodiment of the present disclosure, it was surprisingly found that the polypeptides as described herein confer superior protection against influenza infection, capable of eliciting/boosting neutralizing antibodies against influenza virus, and the polypeptides are soluble, all of which are significant improvements over prior attempts as disclosed in the prior art.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Materials and Methods

Sequence analysis: All non-identical, full-length flu sequences (H1N1:4241 sequences and H5N1:182 sequences, derived from human hosts) were obtained from the NCBI-Flu Database (www.ncbi.nlm.nih.gov/genomnes/FLU/FLU.html). H1N1 sequences were clustered at 99% homology using CD-HIT (Cluster Database at High Identity with Tolerance) to filter-out 465 unique, representative H1N1 sequences which were used for further analysis (Huang Y et al., *Bioinformatics*, 2010, 26(5), 680-682). These H1N1 sequences were multiply aligned using ClustalX (Higgins DG, et al., *Gene*, 1988, 73(1), 237-244). H1N1 (n=465) and H5N1 (n=182) sequences were also simultaneously aligned using ClustalX. The quality score for each column in the alignment file is a measure of residue conservation at that position. The quality scores were binned and mapped onto the crystal structure of H1N1 A/PR/8/34 HA [Protein Data Bank (PDB) ID: 1RU7].

Cloning, expression, and protein purification: The gene sequence of the polypeptide "H1HA10" was synthesized and cloned in the expression vector pET-28a (+)between NdeI and BamH1 restriction sites. Gene sequences corresponding to the trimerization motifs isoleucine-zipper (IZ) and foldon were synthesized with flanking KpnI and HindIII restriction sites. H1HA10-IZ and H1HA10-Foldon, derivatives of the preliminary construct were generated by cloning the trimerization motifs at the C-terminus of H1HA10. The stop-codon in H1HA10 was mutated to generate a unique KpnI restriction site using site-directed mutagenesis to facilitate cloning of the trimerization motifs. Cloning was confirmed by sequencing. Gene sequences corresponding to NCH1HA10-Foldon, pH1HA10-Foldon and H5HA10-Foldon were synthesized and cloned in the expression vector pET-28a (+) between NdeI and HindIII restriction sites. All constructs were codon-optimized for expression in $E.$ $coli.$ The proteins were over-expressed in $E.$ $coli$ BL21 (DE3) cells and purified from the soluble fraction of the cell culture lysate. All proteins in the present disclosure were purified using a similar protocol. Briefly, a single colony of *E. coli* BL21(DE3) transformed with the plasmid of interest was inoculated into 50 ml of Tartoff-Hobbs HiVeg™ media (HiMedia). The primary culture was grown over-night at 37° C. 2 L of Tartoff-Hobbs HiVeg™ media (500 ml×4) (HiMedia) was inoculated with 1% of the primary inoculum and grown at 37° C. until an $OD_{600}$ of ~0.6-0.8 was reached. Cells were then induced with 1 mM isopropyl-β-thiogalactopyranoside (IPTG) and grown for another 12-16 hours at 20° C. Cells were harvested at 5000 g and resuspended in 100 ml of phosphate-buffered saline (PBS, pH 7.4). The cell suspension was lysed by sonication on ice and subsequently centrifuged at 14,000 g. The supernatant was incubated with buffer-equilibrated Ni-NTA resin (GE HealthCare) for 2 hours at 4° C. under mild-mixing conditions to facilitate binding. The protein was eluted using an imidazole gradient (in PBS, pH 7.4) under gravity flow. Fractions containing the protein of interest were pooled and dialysed against PBS (pH 7.4) containing 1mM EDTA. The dialysed protein was concentrated in an Amicon (Millipore) stirred cell apparatus to a final concentration of ~1 mg/ml. Protein purity was assessed by SDS-PAGE and its identity confirmed by ESI-MS.

While we have carried out the process of production of the polypeptides in *E. coli*, a person ordinarily skilled in the art can readily produce the polypeptides as described herein or substantially the same polypeptides in other expression systems such as yeast, plant, and animal using expression system specific promoters and codon optimized DNA sequences that encode the polypeptides as described herein.

Circular Dichroism: Circular dichroism (CD) spectra for all proteins were recorded on a Jasco J-715C spectropolarimeter flushed with nitrogen gas. The concentration for all proteins was ~5-10 μM. Measurements were done at 25° C. in a 1 mm path length quartz cuvette with a scan rate of 50 nm/min, response time of 4 s, and a bandwidth of 2 nm. Each spectrum was an average of five scans. Mean residue ellipticity (MRE) was calculated as described previously (Ganesh C et al., *Biochemistry,* 1997, 36(16), 5020-5028). The protein spectrum was corrected for buffer (PBS, pH 7.4) signals. While we have carried out the measurements for CD spectra for a subset of the polypeptides as described herein, we reasonably expect similar CD spectra for all polypeptides as described herein or for variants of the polypeptides with similar characteristics.

For thermal unfolding experiments, the CD-signal was monitored as a function of temperature. Thermal denaturation of H1HA10-Foldon was monitored at 208 nm, and for H1N1 A/Puerto Rico/8/34 rHA at 215nrn. The buffer used was PBS (pH 7.4). The data was collected between 15° C-90° C. with a 1° C./min gradient and a data pitch of 0.2° C. Band width was 2 nm and response time was 4 s. A quartz cuvette of 1-mm path length was used. The scan was repeated after cooling the samples back-to 15° C. to measure the reversibility of thermal unfolding. While we have carried out the measurements for a subset of the polypeptides as described herein, we reasonably expect similar results for all polypeptides as described herein or for variants of the polypeptides with similar characteristics.

Fluorescence spectroscopy: All fluorescence spectra were recorded at 25° C. on a Jasco FP-6300 spectrofluorimeter. For intrinsic fluorescence measurements, the protein concentration used was in the range of 1-3 μM. The protein samples were excited at 280 nm, and emission was monitored from 300-400 nm. The excitation and emission slit widths were 3 nm and 5 nm, respectively. Each spectrum was an average of five scans. The data was analyzed after buffer correction. Fluorescence measurements were carried out under native conditions in PBS (pH 7.4) or under denaturing conditions of 7M guanidine hydrochloride (GdnCl) in PBS (pH 7.4). While we have carried out the measurements for a subset of the polypeptides as described herein, we reasonably expect similar results for all polypeptides as described herein or for variants of the polypeptides with similar characteristics.

NMR spectroscopy: One-dimensional $^1$H NMR spectra were recorded on an Agilent 600 MHz NMR spectrometer using a triple resonance probe fitted with a z-axis only pulsed field gradient accessory. Spectra were recorded at 25° C. Chemical shifts were referenced to external DSS. A spectral width of 9615.4 Hz was sampled. Solvent suppression was achieved using the excitation sculpting pulse scheme (Hwang T L et al., *J Magn Reson.,* 1995, A 112, 275-279). H1HA10-Foldon protein samples for NMR were prepared in PBS (pH 7.4) (90% $H_2O$:10% $D_2O$). A total of 2048 scans were recorded with a 1 s relaxation delay. Protein sample (H1HA10-Foldon) was prepared in PBS (pH 7.4) (80% $D_2O$:20% $H_2O$) for the hydrogen exchange studies. One-dimensional $^1$H NMR spectra of H1HA10-Foldon were recorded as a function of time over 24 hours at every 2 hour interval. While we have carried out the measurements for a subset of the polypeptides as described herein, we reasonably expect similar results for all polypeptides as described herein or for variants of the polypeptides with similar characteristics.

Gel-Filtration chromatography: The oligomeric status of purified proteins was analyzed under non-denaturing conditions by gel filtration chromatography at room temperature on a Superdex-200 analytical gel filtration column (GE HealthCare). The column was equilibrated with PBS (pH 7.4) and calibrated using broad range molecular weight markers (GE HealthCare). While we have carried out the measurements for a subset of the polypeptides as described herein, we reasonably expect similar results for all polypeptides as described herein or for variants of the polypeptides with similar characteristics.

Proteolysis: Proteolytic digestion of the designed immunogens was carried out using a protease (trypsin)/substrate molar ratio of 1:50. Reduced and carboxamidated ribonuclease A (RCAM-RNase A) was used as a positive control for trypsin activity. Proteolysis was carried out in the presence of 50 mM HEPES (pH 8.0) and 2 mM $CaCl_2$ on ice. Aliquots were collected at various time-points and quenched for trypsin activity with 0.1% formic acid. Samples collected at different time points were analyzed on 12% SDS-PAGE followed by staining with Coomassie Brilliant Blue R250 (Sigma). While we have carried out the measurements for a subset of the polypeptides as described herein, we reasonably expect similar results for all polypeptides as described herein or for variants of the polypeptides with similar characteristics.

Binding affinity studies using Surface Plasmon Resonance (SPR): Binding affinity of the designed immunogens (H1HA10, H1HA10-IZ and H1HA10-Foldon) and full-length H1N1 A/Puerto Rico/8/34 recombinant HA (rHA) (Sino Biological Inc., Beijing, China) to the stem-directed bnAb (CR6261 IgG) or their single-chain variable fragment (scFv) derivatives (F10-scFv and F16v3-scFv) was determined by SPR experiments performed with a Biacore3000 optical biosensor (Biacore, Uppsala, Sweden) at 25° C. Recombinant CR6261 IgG was produced in 293T cells as described previously (Bommakanti G, et al., *J Virol.*, 2012, 86(24), 13434-13444). Plasmids encoding F10-scFv and F16v3-scFv were synthesized (GenScript, USA) based on the published sequence (Sui J, et al., *Nat Struct Mol Biol.*, 2009, 16(3), 265-273; Corti D, et al., *Science*, 2011, 333 (6044), 850-856) and expressed in *E. coli*. 500-750 response units (RU) of the ligand (CR6261 IgG, F10-scFv or F16v3-scFv) was immobilized by standard amine coupling to the surface of a research-grade CM5 chip (GE HealthCare, Uppsala, Sweden). Ovalbumin immobilized sensor channel served as a negative-control for each binding interaction. Multiple concentrations of the analyte were passed over each channel in a running buffer of PBS (pH 7.4) with 0.05% P20 surfactant. Both binding and dissociation events were measured at a flow rate of 30 µl/min. The sensor surface was regenerated after every binding event by repeated washes with 4M $MgCl_2$. Each binding curve was analyzed after correcting for non-specific binding by subtraction of signal obtained from the negative-control flow channel. The concentration of the monomeric fraction of H1HA10 was used for obtaining the kinetic parameters, while for H1HA10-IZ, H1HA10-Foldon, and H1N1 A/PR/8/34 rHA, concentration of the trimeric fraction were used. The kinetic parameters were obtained by globally fitting the data to a simple 1:1 Langmuir interaction model using BIA EVALUATION 3.1 software. Trace-1 was omitted from global fitting while obtaining the kinetic parameters for H1HA10-IZ, since it could not be fitted to a 1:1 interaction model. While we have carried out the measurements for a subset of the polypeptides as described herein, we reasonably expect similar results for all polypeptides as described herein or for variants of the polypeptides with similar characteristics.

Thermal tolerance of H1HA10-Foldon was assessed by its ability to bind CR6261 after heat stress. The protein sample was incubated at 40° C., 60° C. and 80° C. for 1 h in a PCR cycler (BioRad) with heated lid to prevent evaporation. The samples were cooled to 25° C. and binding affinity to CR6261 was determined by SPR experiments as described above. While we have carried out the measurements for a subset of the polypeptides as described herein, we reasonably expect similar results for all polypeptides as described herein or for variants of the polypeptides with similar characteristics.

Pull down assay: The ability of H1HA10-Foldon to form a stable complex with the bnAb CR6261 IgG was further confirmed in a pull-down assay. CR6261 and H1HA10-Foldon were mixed together at different molar ratios and incubated for 2 h at 4° C. Buffer (PBS, pH 7.4) equilibrated Protein-G (GE HealthCare) beads were added to the complex and incubated for 1 h to specifically pull down CR6261 IgG. The beads were spun down at 3000 g for 15 mins at 4° C. The unbound supernatant was separated and the beads were washed with PBS (pH 7.4). The antibody bound to the beads was eluted with 100 mM Glycine HCl (pH 3.0). The eluted fractions were neutralized with 1M Tris HCl (pH 9.0). The unbound and eluted fractions were subsequently analyzed by SDS-PAGE. While we have carried out the measurements for a subset of the polypeptides as described herein, we reasonably expect similar results for all polypeptides as described herein or for variants of the polypeptides with similar characteristics.

Immunization and challenge studies: Female BALB/c mice (4-5 weeks old) (Taconic Farms, Inc., Germantown, N.Y.) were maintained at the animal facilities of Merck Research Laboratories. The study design was approved by the Merck Research Laboratories Institutional Animal Care and Use Committee. Mice (10/group) were immunized intramuscularly with 20 µg of test immunogen along with 100 µg CpG7909 adjuvant (TriLink BioTechnologies, San Diego, Calif.) at days 0 (prime) and 28 (boost). Naïve (buffer only) mice and adjuvant-treated mice were used as controls. Serum sample obtained from tail vein venipuncture were collected in Microtainer serum separator tubes (BD Biosciences, Franklin Lakes, N.J.) 21 days after the prime and 14 days post boost from all the mice. 21 days after the secondary immunization, mice were anesthetized with ketamine/xylazine and challenged intranasally with $ILD_{90}$ of mouse-adapted H1N1 A/PR/8/34 virus in 20 µL of PBS. In order to test for protection against a higher dose of the virus, one group of mice primed and boosted with H1HA10-Foldon was challenged with $2LD_{90}$ of homologous A/PR/8/34 virus. The ability of NCH1HA10-Foldon, pH1HA10-Foldon and H5HA10-Foldon to confer cross-protection was evaluated against a stringent $2LD_{90}$ heterologous H1N1 A/PR/8/34 virus challenge. Another group of mice (n=10) immunized with pH1HA10-Foldon were challenged with $2LD_{90}$ heterologous, mice-adapted H3N2 A/HK/68 virus. Survival and weight change of the challenged mice were monitored daily for 14 days post challenge. At each time point, all surviving mice of a group were weighed together and the mean weight calculated. Errors in the mean weight were estimated from three repeated measurements of the mean weight of the same number of healthy mice. While we have carried out the measurements for a subset of the polypeptides as described herein, we reasonably expect similar results for all polypeptides as described herein or for variants of the polypeptides with similar characteristics.

Determination of serum antibody titers: Antibody-titers against test immunogens were determined by ELISA. Briefly, test immunogens were coated on 96-well plates (Thermo Fisher Scientific, Rochester, N.Y.) at 4 µg/ml in 50 µl PBS at 4° C. overnight. Plates were then washed with PBS containing 0.05%Tween-20 (PBST) and blocked with 3% skim milk in PBST for 1 h. 100 µl of the antisera raised against the test immunogens was diluted in a 4-fold series in milk-PBST and added to each well. Plates were incubated for 2h at room temperature followed by washes with PBST. 50 µl of HRP-conjugated goat anti-mouse IgG (H+L) secondary antibody in milk-PBST was added to each well at a predetermined dilution (1:5000) and incubated at room temperature for 1 h. Plates were washed with PBST followed by development with 100 µl per well of the substrate 3, 3',5,5'-tetramethylbenzidine (TMB) solution and stopped after 3-5 min of development with 100 µl per well of the stop solution for TMB. OD at 450 nm was measured and the antibody titer was defined as the reciprocal of the highest dilution that gave an OD value above the mean plus 2 standard deviations of control wells. While we have carried out the measurements for a subset of the polypeptides as described herein, we reasonably expect similar results for all polypeptides as described herein or for variants of the polypeptides with similar characteristics.

Binding of antisera to recombinant polypeptides: Binding of antisera raised against the test immunogens to several rHA proteins was determined by ELISA. Briefly, mammalian-expressed rHA proteins (H1N1 A/Puerto Rico/8/34, H1N1 A/California/04/2009, H1N1 A/Brisbane/59/2007, H5N1 A/Viet Nam/1203/2004, H3N2 A/Aichi/2/68, H3N2 A/Brisbane/10/07 from Sino Biological Inc., Beijing, China) were coated on 96-well plates at 2.5 μg/ml in 50 μl PBS at 4° C. overnight. Ovalbumin (125 ng/well) coated wells were used as a negative control. Plates were washed with PBST (PBS containing 0.05%Tween-20) and blocked with 1% BSA in PBST (PBSB). Antisera were then added to each well at a starting dilution of 1:100 followed by a 4-fold dilution series and incubated for 2 h. Plates were washed with PBST. Alkaline phosphatase (ALP)-conjugated goat anti-mouse secondary antibody in PBSB was added to each well at a predetermined dilution (1:10000) and incubated at room temperature for 2 h. Plates were washed and developed using the chromogenic substrate p-nitrophenyl phosphate (Sigma). Plates were read at 405 nm (SPECTRAmax Plus 384, Molecular Devices, USA). Antibody titer was defined as the reciprocal of the highest dilution that gave an OD value above the mean plus 2 standard deviations of control wells. While we have carried out the measurements for a subset of the polypeptides as described herein, we reasonably expect similar results for all polypeptides as described herein or for variants of the polypeptides with similar characteristics.

Competition ELISA: Competition ELISA between the antisera raised against the test immunogens and the bnAb CR6261 IgG was carried out as described elsewhere (Shembekar N, et al., *PLoS One*, 2013, 8(1), e55516). Briefly, 96-well half area plates (Corning Incorporated, NY) were coated with 3 μg of pandemic H1N1 A/California/04/2009 rHA (Sino Biological Inc., Beijing, China) in 50 μl PBS and kept overnight at 4° C. Ovalbumin (3 μg) coated wells were used as negative control for antisera binding. Plates were washed with PBST and blocked for 1 h with PBSB. 25 μl of antisera were added to each well starting at 1:100 dilution followed by a 3-fold serial dilution in PBSB. As a control for non-specific competition, a previously characterized head-specific neutralizing monoclonal antibody (MAb) IgG MA2077 was used. 25 μl of MAb MA2077 was added to each well starting at a concentration of 2 mg/ml followed by 3-fold serial dilutions. After 2 h of incubation, the plates were washed and blocked with PBSB for 15 mins. CR6261 was then added to each well at a fixed concentration (300 ng/ml) as determined from the titration curve of CR6261 with pandemic H1N1 rHA. After 2 h of incubation with CR6261, the plates were washed with PBST. The wells were then probed with 25 μl of ALP-conjugated goat anti-human antibody (Sigma) at a predetermined dilution (1:10000) to detect the bound CR6261. The plates were washed and developed using the chromogenic substrate p-nitrophenyl phosphate (Sigma). The optical density was measured at 405 nm (SPECTRAmax Plus 384, Molecular Devices, USA). Percent competition was calculated as follows: % Competition=[(A−P)/A]×100, where A is the signal of CR6261 binding to rHA in the absence of anti-serum and P is the binding signal of CR6261 to rHA in the presence of antiserum (Bommakanti G, et al., *J Virol.*, 2012, 86(24), 13434-13444). While we have carried out the measurements for a subset of the polypeptides as described herein, we reasonably expect similar results for all polypeptides as described herein or for variants of the polypeptides with similar characteristics.

Statistical analysis: Differences in antibody titers and mean fractional body weights of surviving mice between different groups were analyzed by analysis of variance and Student's t-test. The fractional body weight of mice is calculated relative to their starting body weight. Differences in survival were calculated by Kaplan-Meier survival analysis with the log rank significance test.

Example 2

Results (Immunogen/Polypeptide Design)

Antigenic differences between the HA surface glycoprotein of various influenza A viruses provides the basis for classification into 18 subtypes (H1-H18) (Tong S, et al., *PLoS Pathog.*, 2013, 9(10), e1003657). Wide diversity and rapid antigenic variation of HA remains the principal challenge to the development of potent vaccines. Targeting conserved regions of HA offers a promising strategy to combat viral evolution and escape. We analyzed a large dataset (H1N1: 4241 and H5N1: 182 sequences) of Group-1 influenza virus sequences to identify conserved targets on HA. Consistent with previous results (Ellebedy AH et al., *Front Immunol.*, 2012, 3, 5), the HA stem is more conserved as opposed to the highly-variable globular head domain. The residue conservation across all full-length, human isolates of H1 HA and Group-1 HA was mapped onto the crystal structure of H1N1 A/PR/8/34 HA (PDB ID: 1RU7(Gamblin S J, et al., *Science*, 2004, 303(5665), 1838-1842). The HA stem comprising the epitope of bnAbs is therefore a plausible target for developing a broadly protective vaccine (Harris A K, et al., *Proc Natl Acad Sci USA*, 2013, 110(12), 4592-4597).

Mimicking the epitope of these stem-directed bnAbs in a native, pre-fusion conformation in a 'headless' stem immunogen is challenging because of the metastable conformation of HA. The HA2-subunit when expressed independently adopts the low-pH conformation spontaneously (Chen J, et al., *Proc Nail Acad Sci USA*, 1995, 92(26), 12205-12209). Extensive rearrangement at low-pH displaces the A-helix by over 100 Å (Skehel J J et al., *Annu Rev Biochem.*, 2000, 69, 531-569) disrupting the conformation-specific epitope of these bnAbs.

In order to enhance the immune response to the epitope of the HA stem-directed bnAbs like CR6261, F10 and F16v3 (Ekiert D C, et al., *Science*, 2009, 324(5924), 246-251; Sui J, et al., *Nat Struct Mol Biol.*, 2009, 16(3), 265-273; Corti D, et al., *Science*, 2011, 333(6044), 850-856), a protein-minimization approach to refine the previously reported HA stem immunogens, H1HA6 and H1HA0HA6 was adopted. These HA stem immunogens consisted of the entire stem region of HA and were 258 (H1HA6) and 243 (H1HA0HA6) residues in length. Smaller 'headless' HA stem immunogens that contained the above epitope were designed from influenza A (H1N1) A/Puerto Rico/8/34 subtype. We analyzed the interaction network of residues in the antibody-footprint of these bnAbs with the rest of HA using the in-house software PREDBURASA as described previously (Sharma D, et al., *Biochemistry*, 2005, 44(49), 16192-16202). Briefly, the accessible surface area (ASA) of every residue in HA was calculated in the absence and presence of at least 3-residue long stretches of the CR6261 antibody footprint ($32_1$-$36_1$, $292_1$-$294_1$, $18_2$-$21_2$, $36_2$-$56_2$), covering ~95% of the CR6261-epitope. Residues belonging to either HA1 or HA2 subunits are distinguished by subscripts 1 or 2 respectively. An residues of HA which had a total side-chain ASA difference of ≥5 Å² in the aforementioned calculations were identified as interacting 'network' residues. We repeated the PREDBURASA calculations now including the 'network' residues to identify HA stem fragments defined by stable breakpoints with optimal termini distances, having minimalistic interactions with the rest of HA. Residue fragments $18_1$-$41_1$ (24 amino acid residues), $290_1$-$323_1$ (34 amino acid residues) and $41_2$-$113_2$ (73 amino acid residues) were included in H1HA10 (FIG. 1). H1HA10 includes ~80% of the CR6261 antibody-footprint. H1HA10 is 139 residues in length and is therefore ~46% smaller than the full-length HA stem immunogen described previously (Bommakanti G, et al., *J Virol.*, 2012, 86(24), 13434-13444). The newly generated exposed hydrophobic patches in H1HA10 due to interactions lost with the rest of HA were mutated using the software ROSETTA DESIGN (Version 3.0) to minimize In order to assess the ability of stem immunogens to confer cross-protection, constructs similar to H1HA10-Foldon were designed from unmatched, highly drifted influenza strains and tested against heterologous PR8-virus challenge in mice. Constructs from other strains [H1N1 A/New Caledonia/20/99 (NCH1HA10-Foldon), H1N1 A/California/04/2009 (pH1HA10-Foldon), and H5N1 A/Viet Nam/1203/2004 (H5HA10-Foldon)] were designed using a facile strategy. A simplistic, pair-wise sequence alignment which can guide immunogen design emphasizes the utility of the design. The hydrophobic residues mutated in H1HA10 to mask the newly generated hydrophobic patches are identical/similar within a subtype; therefore, analogous mutations can be included in H1HA10-like designs from other strains.

Table 1 represents the residue conservation within influenza A H1N1 subtype (representative protein sequence)

| Strain | % identity with full-length A/Puerto Rico/8/34 HA | % identity with H1HA10 (A/Puerto Rico/8/34) | % identity within H1HA10-fragments (A/Puerto Rico/8/34) | | |
|---|---|---|---|---|---|
| | | | HA1 ($18_1$-$41_1$) | HA1 ($290_1$-$323_1$) | HA2 ($41_2$-$113_2$) |
| A/South Carolina/1/1918 | 89 | 95 | 100 | 94 | 93 |
| A/WSN/1933 | 91 | 93 | 83 | 94 | 96 |
| A/Bellamy/1942 | 94 | 97 | 96 | 97 | 97 |
| A/CHR/157/83 | 91 | 96 | 96 | 94 | 97 |
| A/Taiwan/4845/1999 | 89 | 95 | 86 | 97 | 96 |
| A/Oklahoma/03/2008 | 86 | 95 | 92 | 97 | 96 |
| A/Texas/45034157/2009 [a] | 82 | 89 | 96 | 79 | 92 |
| A/Alabama/03/2010 [a] | 82 | 89 | 96 | 79 | 92 |
| A/Kenya/151/2011 [a] | 81 | 89 | 96 | 79 | 92 | potential protein aggregation. A similar approach has been previously used by us to design stable influenza and HIV-immunogens and inhibitors (Bommakanti G, et al., *J Virol.*, 2012, 86(24), 13434-13444; Bhattacharyya S, et al., *J Biol Chem.*, 2013, 288(14), 9815-9825; Saha P, et al., *Biochemistry*, 2011, 50(37), 7891-7900). The following mutations were incorporated to mask the hydrophobic patch: $1298_1$T, $V301_1$T, $1303_1$N, $V66_2$T and $F110_2$A (FIG. 1). $Cys281_1$ and $Cys306_1$ form an intramolecular disulfide bond in full-length HA. Since $Cys281_1$ was not incorporated in our design, we mutated $Cys306_1$ to Ser to prevent incorrect, intermolecular disulfide bond formation. Low-pH conformation destabilizing mutations: $F63_2$D and $L73_2$D which were previously characterized (Bommakanti G, et al., *J Virol.*, 2012, 86(24), 13434-13444), were also incorporated in the design. Residues $S54_2$ and $N82_2$ present in the PR8 HA crystal structure (PDB ID: 1RU7) were replaced in H1HA10 with the most commonly occurring residue ($T54_2$ and $K82_2$) at that position among all the available H1N1 A/Puerto Rico/8/34 sequences deposited with the NCB1-Flu Database. None of the introduced mutations were in the epitopes of the previously reported stem-directed bnAbs CR6261, F10 or F16v3. These independent HA fragments were connected by flexible, soluble linkers of appropriate length as described previously (Varadarajan R, et al., *J Virol.*, 2005, 79(3), 1713-1723). Also to promote the formation of trimer derivatives of H1HA10 with C-terminal trimerization motifs connected by flexible linkers were made. The parallel, coiled-coil trimerization motif Ile-zipper (IZ) (Suzuki K et al., *Protein Eng.*, 1998, 11(11), 1051-1055) was used in H1HA10-IZ. H1HA10-Foldon had the globular, (β-rich trimerization motif 'Toldon' (Guthe S, et al., *J Mol Biol.*, 2004, 337(4), 905-915).

Example 3

Results (Protein Purification and Biophysical Characterization of HA Stem Immunogens)

Protein solubility is a coarse indicator of proper folding and remains a crucial problem in heterologous expression systems. HA fragments expressed previously in *E. coli* formed inclusion body aggregates and required refolding (Bommakanti G, et al., *J Virol.*, 2012, 86(24), 13434-13444; Song L, et al., *PLoS One*, 2008, 3(5), e2257). In contrast, all the designed immunogens/polypeptides as described herein, expressed in *E. coli* BL21(DE3) cells were purified from the soluble fraction of the cell culture lysate, suggesting proper folding and validation of the design protocol. The protein yields were about 10-15 mg/liter culture using unoptimized shake-flask cultures and were purified using a single, affinity-purification step.

Figure 2:
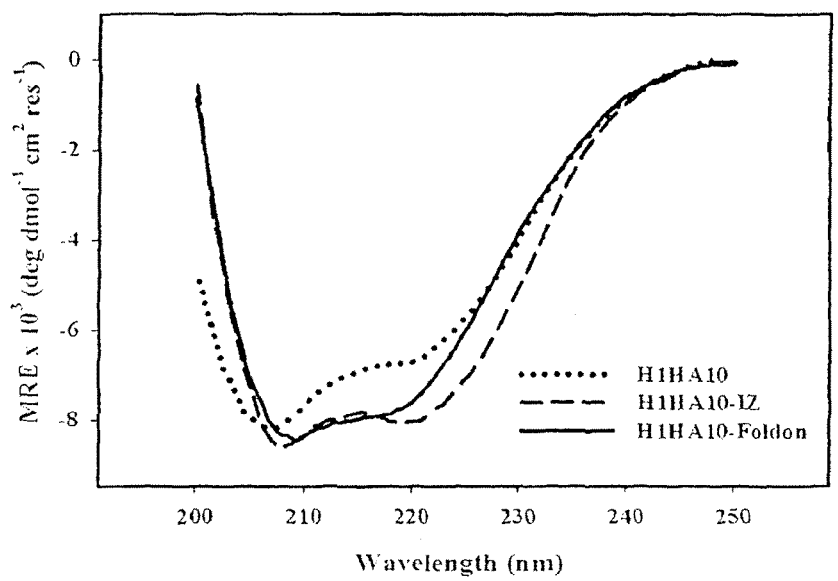
Figure 10:
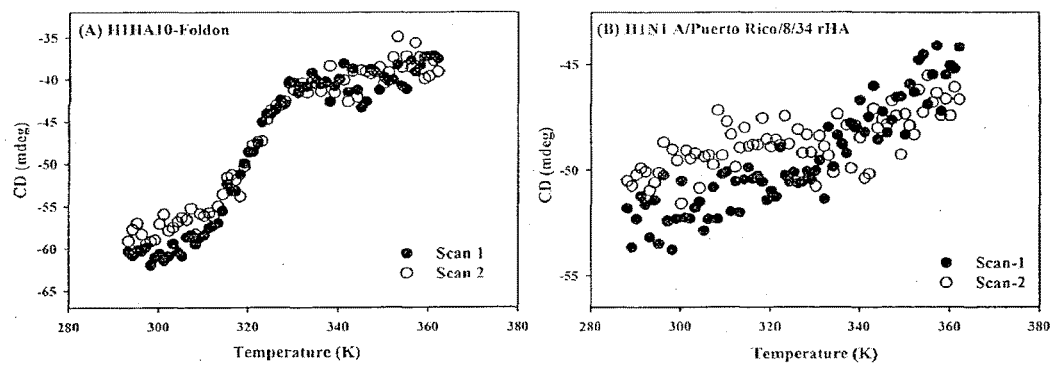
Figure 11:
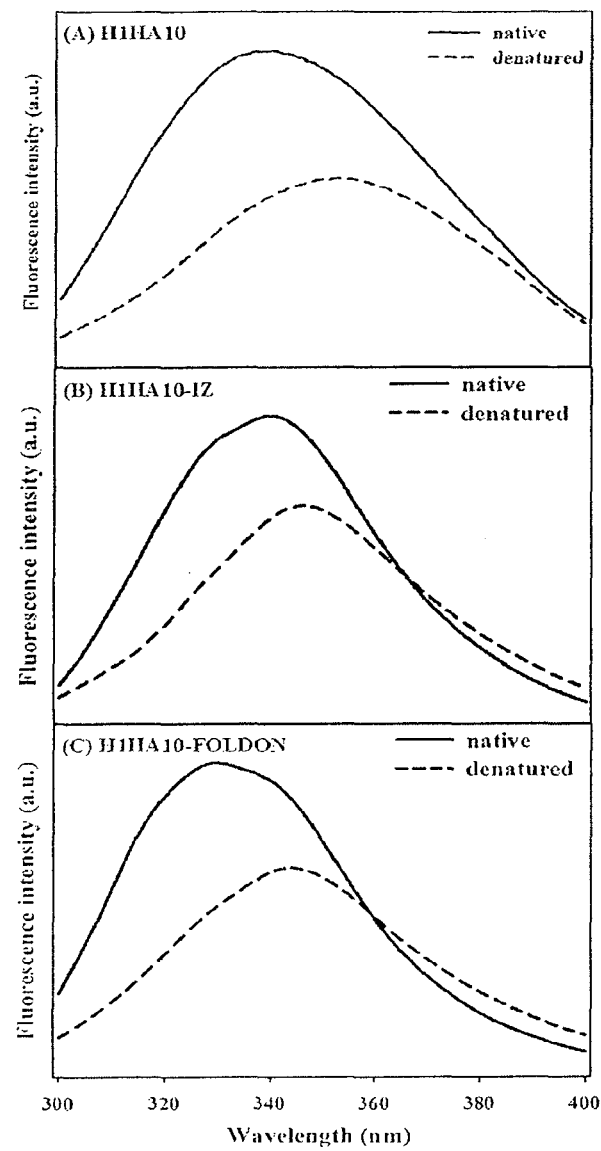

CD-spectra indicated that all the proteins were folded and predominantly a-helical as expected. The trimerization motifs assist in the folding of H1HA10. H1HA10-IZ and H1HA10-Foldon are more helical than the parent construct H1HA10 as observed from the double minima at 208 nm and 222 nm (FIG. 2). The thermal stability of H1HA10-Foldon was monitored using CD. H1HA10-Foldon showed a reversible and co-operative unfolding thermal melt profile with an apparent transition mid-point ($T_m$) of ~323K (50° C.) at a protein concentration (in monomer units) of ~15 µM. Since the folded protein is a trimer and the unfolded protein is a likely to be a monomer, the $T_m$ is expected to be concentration dependant. Consecutive scans recorded after cooling the sample back-to 15° C. overlapped well with each other. (FIG. 10A). In contrast, the full-length H1N1 A/Puerto Rico/8/34 rHA showed a broad transition without clear baselines and it was therefore not possible to estimate a $T_m$. The rescan showed no transition, indicating that thermal denaturation for rHA is irreversible (FIG. 10B). Intrinsic tryptophan fluorescence measurements also affirmed a folded, native structure for H1HA10 and its derivatives. All proteins showed a significant red-shift in the emission maxima upon denaturation with GdnCl (FIG. 11A-C).

Figure 3:
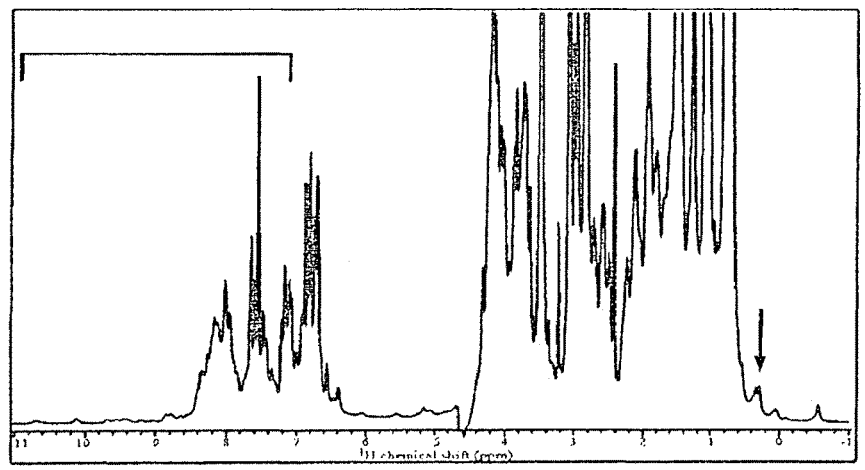

Furthermore, the one-dimensional $^1$H-NMR spectrum of H1HA10-foldon exhibits solution properties characteristic of a well-folded protein molecule. The presence of resolved resonance lines that appear in the downfield (9-11 ppm) and the upfield (0.5--1.0 ppm) regions of the spectrum are clear indicators that the molecule adopts a stable tertiary structure (FIG. 3). The upfield shifted signals are those of methyl protons that are spatially proximal to aromatic rings in the interior of the protein (hydrophobic core). The conformational stability of the folded state of H1HA10-Foldon was further probed by hydrogen exchange studies. The slow exchange of the amide protons in the downfield (9-11 ppm) region of the one-dimensional $^1$H-NMR spectrum is suggestive of a well-packed molecule.

Figure 5:
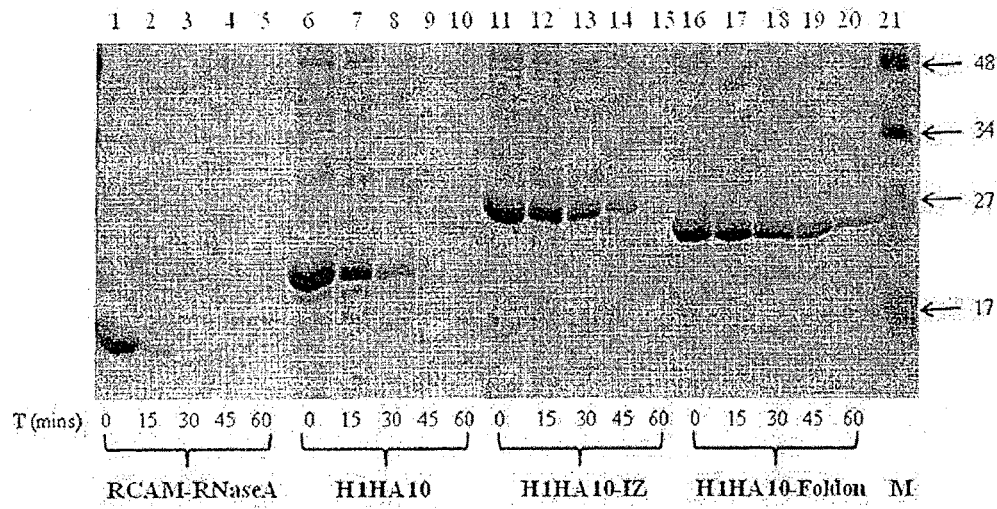

IZ<H1HA10-Foldon. Proteolysis confirmed a compact, folded conformation for H1HA10-Foldon (FIG. 5).

Example 5

Results ("Headless" Stem Immunogens Bind Confirmation Specific BnAbs)

Stem-directed bnAbs like CR6261, F10 and F16v3 bind the native, neutral-pH conformation of HA with high affinity (Ekiert DC, et al., Science, 2009, 324(5924), 246-251; Sui J, et al., Nat Struct Mol Biol., 2009, 16(3), 265-273; Corti D, et al., Science, 2011, 333(6044), 850-856). Epitopes of these bnAbs are disrupted in the low-pH, fusion-competent conformation of HA. Therefore, the ability of stem-derived immunogens to bind these bnAbs offers a robust validation of their conformation.

Binding of the designed 'headless' stem immunogens to the bnAbs was determined by SPR. H1HA10 bound IgG CR6261 with sub-micromolar affinity (315.4±14.5 nM) (Table 2, FIG. 12A).

TABLE 2

| Immunogen | Ligand[a] | $k_{on}$ (M$^{-1}$s$^{-1}$) | $k_{off}$ (s$^{-1}$) | $K_D$ (nM) |
|---|---|---|---|---|
| H1HA10 | CR6261-IgG | 2.49 ± 0.08 × 10$^4$ | 7.85 ± 0.09 × 10$^{-3}$ | 315.4 ± 14.5 |
| H1HA10-IZ | CR6261-IgG | 6.55 ± 0.51 × 10$^4$ | 4.84 ± 0.11 × 10$^{-3}$ | 73.9 ± 2.3 |
| H1HA10-Foldon | CR6261-IgG | 3.72 ± 0.22 × 10$^4$ | 1.95 ± 0.19 × 10$^{-3}$ | 52.4 ± 1.8[b] |
| | F10-scFv | 1.54 ± 0.14 × 10$^5$ | 1.50 ± 0.20 × 10$^{-3}$ | 9.8 ± 2.1 |
| | FI6v3-scFv | 1.69 ± 0.53 × 10$^5$ | 2.05 ± 0.12 × 10$^{-3}$ | 12.1 ± 3.4 |
| H1 A/PR/8/34 rHA | CR6261-IgG | 2.89 ± 0.02 × 10$^5$ | 2.58 ± 0.08 × 10$^{-3}$ | 8.9 ± 0.3 |
| | F10-scFv | 4.15 ± 0.61 × 10$^5$ | 1.21 ± 0.21 × 10$^{-3}$ | 2.9 ± 0.9 |
| | FI6v3-scFv | 2.45 ± 0.06 × 10$^5$ | 2.16 ± 0.27 × 10$^{-3}$ | 8.8 ± 1.1 |

Example 4

Results (H1HA10-Foldon is a Homogenous Trimer in Solution and Resistant to Proteolysis)

Figure 4:
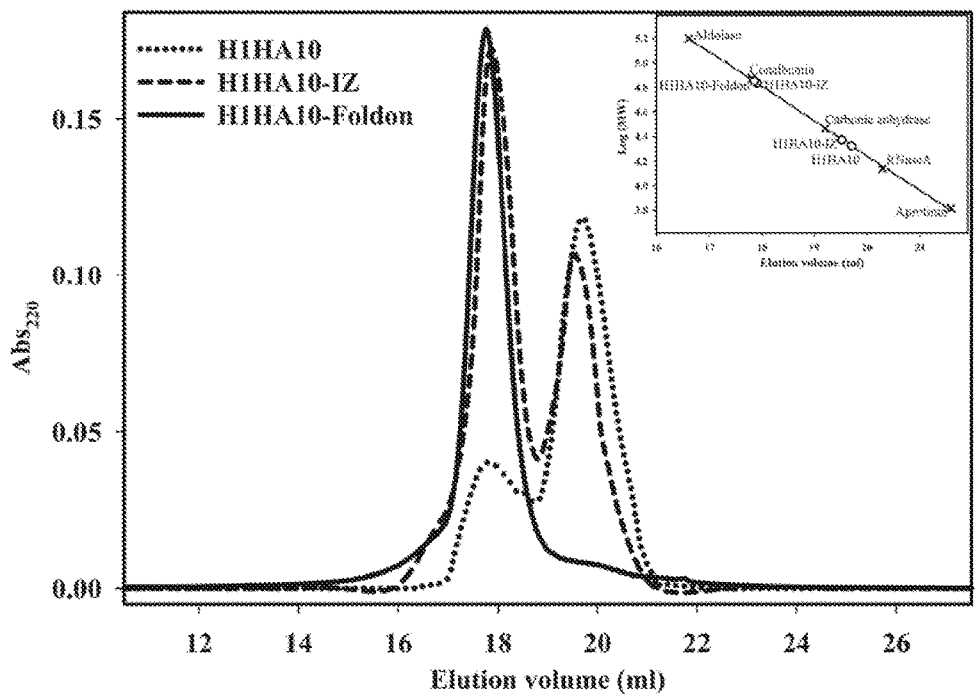

The long central α-helices (LAH) located in the HA stem assemble together into a parallel, trimeric coiled-coil promoting oligomerization. The oligormeric state of the designed immunogens was probed by analytical gel-filtration chromatography under native conditions. H1HA10 eluted predominantly as a monomer and a minor trimeric peak. This was probably because in the absence of the trans-membrane (TM) domain of HA, the trimer is not stable (Copeland C S et al., J Cell Biol., 1986, 103(4), 1179-1191). It has previously been demonstrated that trimerization motifs facilitate oligomerization in the absence of the HA TM domain (Stevens J, et al., Science, 2006, 312(5772), 404-410). Both IZ and Foldon trimerization sequences aided in trimerization of H1HA10. H1HA10-IZ formed a mixture of stable trimeric (~65%) and monomeric (~35%) conformers in solution which did not re-equilibrate when partitioned. H1HA10-Foldon eluted exclusively as a trimer in solution (FIG. 4). In contrast to previously designed immunogens H1HA6 and H1HA0HA6 which contain the entire stem domain (Bommakanti G, et al., J Virol., 2012, 86(24), 13434-13444), none of the proteins characterized in the present dislcosure were aggregation prone. Gel-filtration studies indicate that we have effectively resurfaced exposed hydrophobic patches in our designed constructs.

Misfolded proteins having disordered sectors are subjected to increased proteolysis. H1HA10 showed limited resistance to proteolysis (trypsin digestion) compared to a control unfolded protein (RCAM-RNaseA). Proteolytic stability increased in the order H1HA10<H1HA10-

Figure 12:
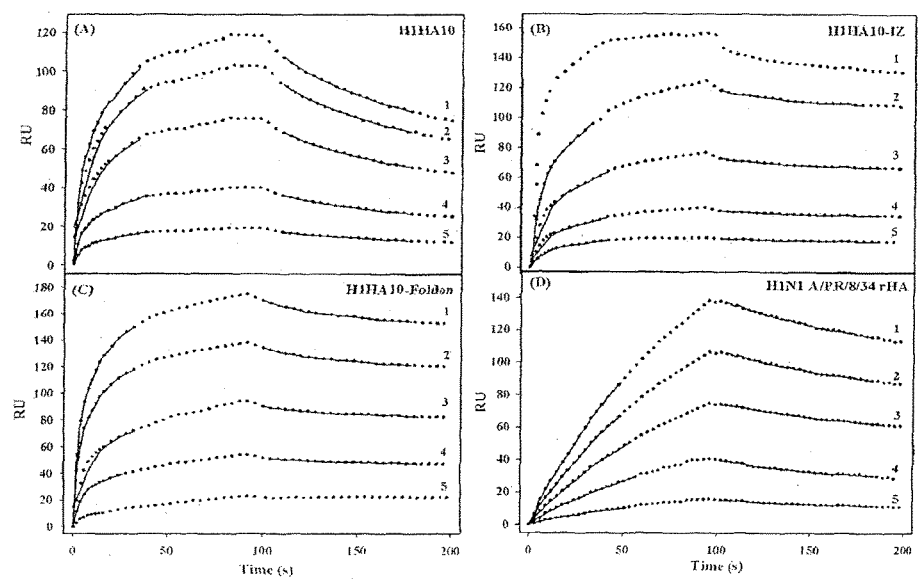

As previously mentioned, H1HA10 has ~80% of the antibody-footprint. H1HA10 though folded, is monomeric and not particularly compact as implied from proteolysis. These factors may contribute to the high $k_{off}$ which would decrease the binding affinity (Table 2). Derivatives of H1HA10, which had improved biophysical and biochemical properties had considerably tighter binding to CR6261. H1HA10-IZ had an equilibrium dissociation constant ($K_D$) of 73.9±2.3 nM. The conformational heterogeneity of H1HA10-IZ in solution may possibly lead to the observed biphasic binding to CR6261 at higher concentrations (FIG. 12B) as observed previously with the HA stem immunogen H1HA6 (Bommakanti G, et al., J Virol., 2012, 86(24), 13434-13444). H1HA10-Foldon, which assembles into a homogenous trimer in solution, bound CR6261 with the highest affinity among the designed stem immunogens (52.4±1.8 nM) (FIG. 12C). Although H1HA10-Foldon binds CR6261 with ~6-fold weaker affinity than full-length PR8 rHA (8.9±0.3 nM) (FIG. 12D) (Table 2), it is a significant improvement over the previously reported stem immunogen H1HA6 (~260nM) which comprised the entire HA stem with the complete CR6261-epitope.

Binding of H1HA10-Foldon to the scFv-derivatives of other stem-directed bnAbs (F10 and F16v3) was also determined to confirm the native, pre-fusion HA-like conformation of H1HA10-Foldon. The slower off-rates for both H1HA10-Foldon and PR8 rHA result in a higher affinity to F10-scFV in comparison to IgG CR6261 (Table 2). The $K_D$ of H1HA10-Foldon binding to F10-scFv was 9.8±2.1 nM, about ~3-fold weaker than full-length PR8 rHA (2.9±0.9 nM). H1HA10-Foldon also bound F16v3 (the pan-influenza binding antibody) with a low $K_D$ of 12.1±3.4 nM (Table1).

Thermal tolerance, a pharmaceutically relevant parameter was assessed by determining the $K_D$ of H1HA10-Foldon binding to CR6261 after prolonged heat stress. H1HA10-Foldon bound CR6261 with a $K_D$ of 71.6±0.5 nM even after incubating the protein at 80° C. for 1 h.

The specificity of H1HA10-Foldon binding to IgG CR6261 was also confirmed in a pull-down assay. Protein-G beads specific for human IgG CR6261 were used to pull down the antibody-antigen complex.

Example 6

Results (HA Stem Immunogens Elicit Broadly Cross-reactive, Anti-influenza Antibodies)

Figure 6:
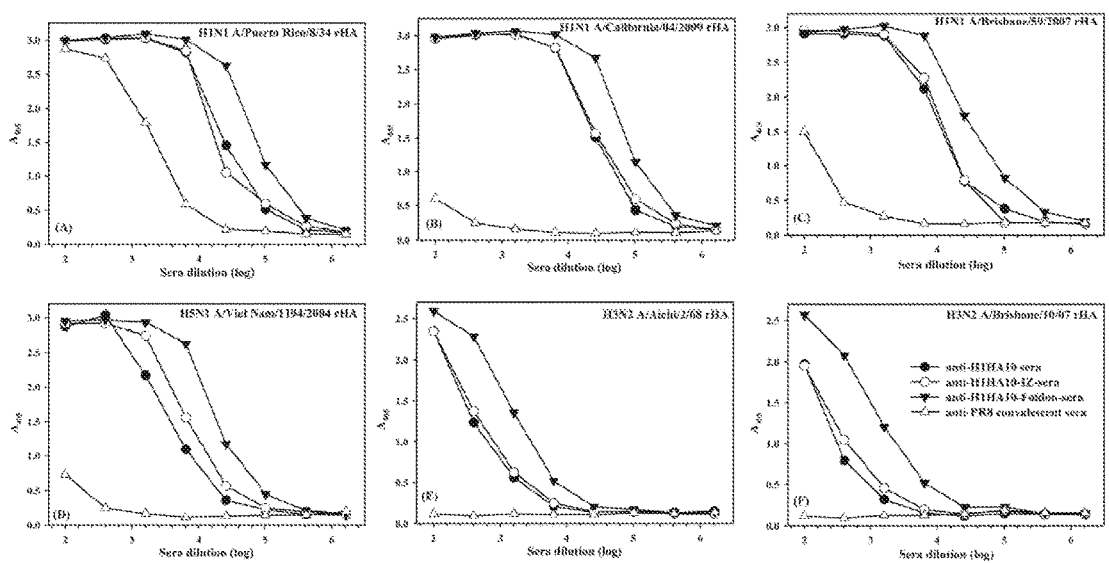

During natural infection, the immunodominant head domain steers the immune response away from the conserved stem Kwong P D et al., Nat Immunol., 2009, 10(6), 573-578). This is probably the reason why there are low/undetectable cross-reactive antibodies in the anti-PR8 convalescent sera. In contrast, high titers of cross-reactive antibodies are elicited by the stem domain immunogens of the present disclosure (FIG. 6) confirming that the immunogens have adopted a native-like, neutral-pH conformation. H1HA10-Foldon elicited the highest cross-reactive antibody titers (in the range of 409,600-1,638,400) with Group-1 HAs (FIG. 6A-D). H1HA10-Foldon bound the pan-influenza neutralizing antibody F16v3 with high affinity, which prompted us to examine the ability of anti-H1HA10-Foldon sera to bind Group-2 HAs. Interestingly, H1HA10-Foldon elicited moderate titers (25,600) of cross-reactive antibodies against (Group-2) H3 HAs (FIG. 6E, F). However, additional design optimization incorporating the sequence variation information amongst the stem of all HA-subtypes will be essential to formulate an immunogen that can elicit a truly 'universal' response.

Figure 7:
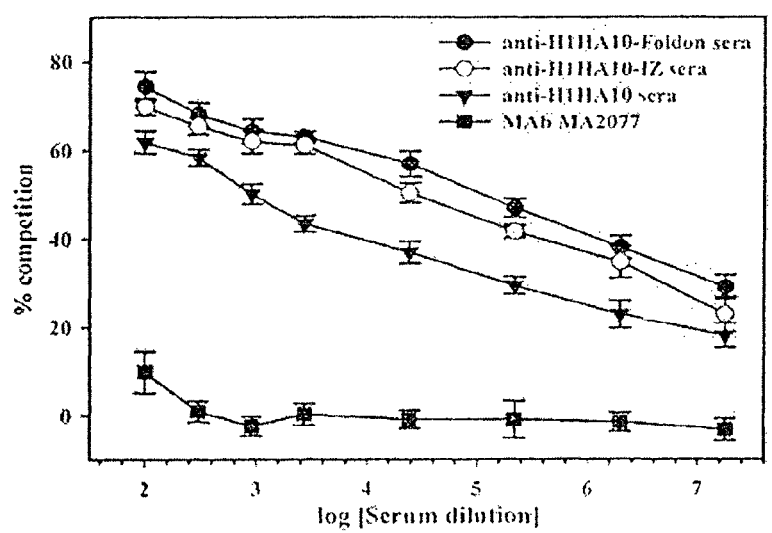

Antibodies elicited by the HA stem immunogens probably mediate virus neutralization by inhibiting virus-host cell membrane fusion as inferred from their ability to compete with the stem-directed bnAb IgG-CR6261 for binding to H1N1A/California/04/2009 rHA (FIG. 7). The sera elicited against H1HA10-Foldon showed maximum competition with CR6261, in accordance with the improved biophysical/biochemical properties of the immunogen. The competition assay demonstrates the presence of CR6261-like antibodies following immunization with 'headless' stem immunogens. As a control, the nAb MA2077 which binds at the 'Sa' antigenic site on H1N1 A/California/04/2009 HA9(Shembekar N, et al., PLoS One, 2013, 8(1), e55516) failed to compete with CR6261.

The sera were not tested in a hemagglutinin inhibition (H1) assay because the stem-directed bnAbs mediate neutralization by inhibiting membrane-fusion and not by blocking the virus from binding to receptors on the host cells (Okuno Y et al., J Virol., 1994, 68(1), 517-520).

Example 7

Results (H1HA10-Foldon Completely Protects Against a Lethal Homologous Virus Challenge)

Figure 8:
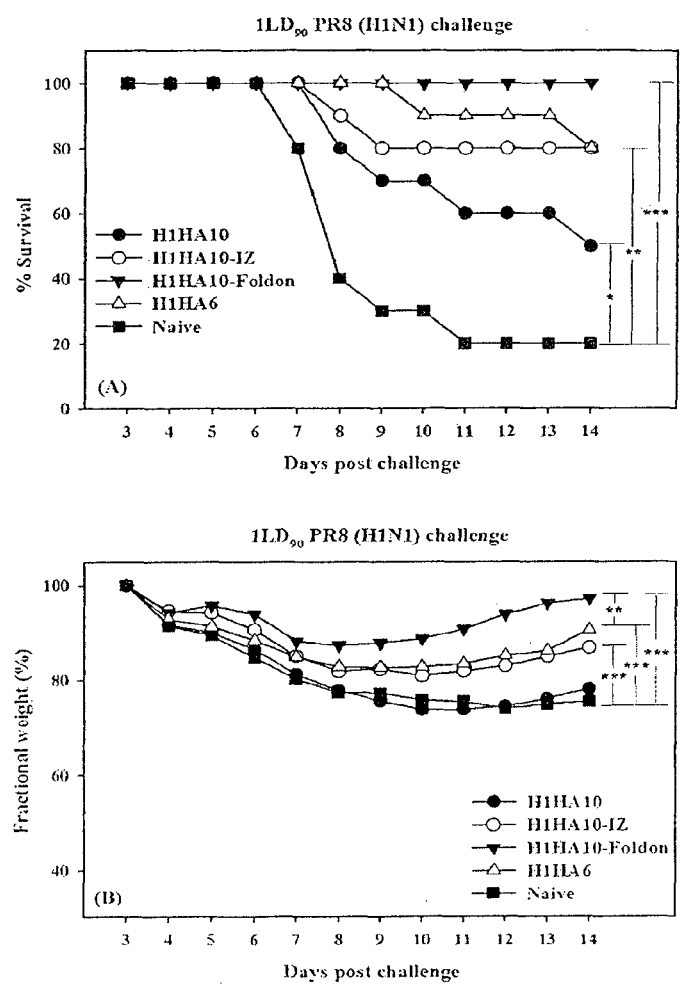
Figure 9:
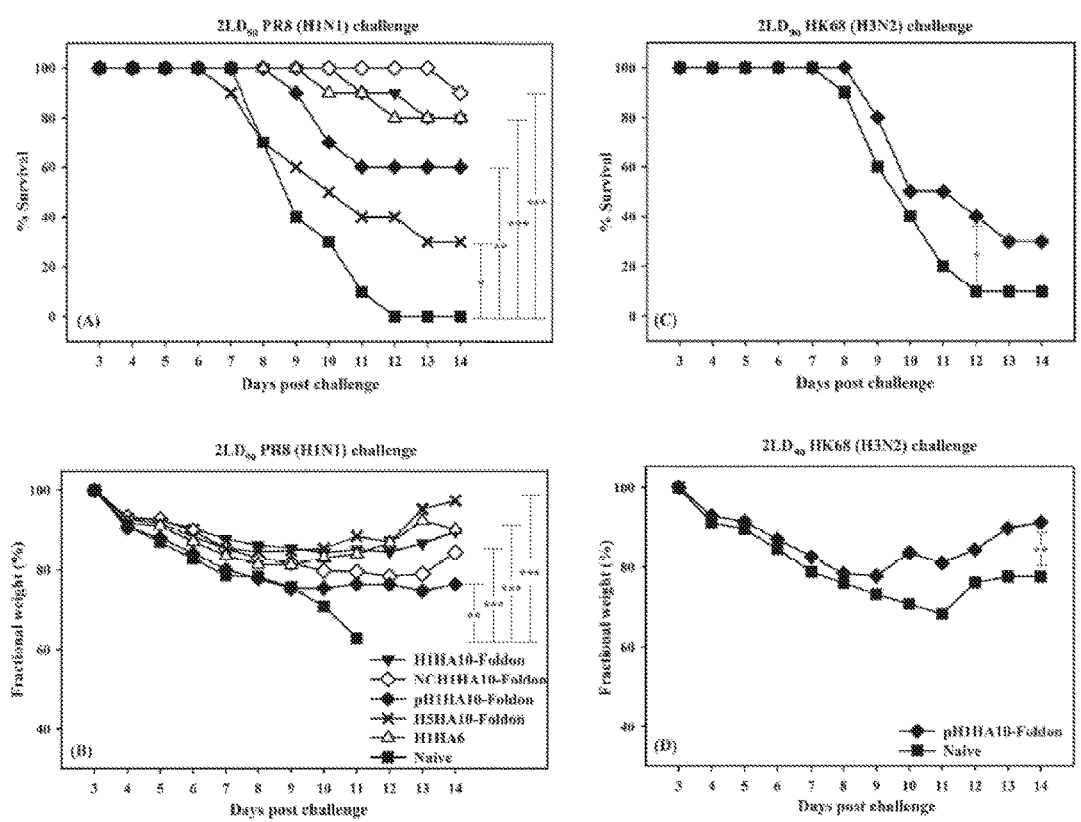

All the 'headless' constructs elicited a robust immune response in mice with high serum antibody self-titers (>1, 638,400). 21-days post-secondary immunization, mice were challenged intranasally with a lethal dose (1 $LD_{90}$) of homologous PR8-virus. The challenged mice showed significant weight recovery by the end of the observation period after initial weight loss (FIG. 8B). The monomeric immunogen H1HA10 conferred 50% protection, while its compact, trimeric-derivative H1HA10-Foldon protected mice completely from a lethal homologous virus challenge (FIG. 8A). Notably, immunization with H1HA10-Foldon gave improved protection in comparison to a previously reported stem-immunogen, H1HA6 (Bommakanti G, et al., J Virol., 2012, 86(24), 13434-13444). The extent of weight loss was also slightly lower for mice immunized with H1HA10-Foldon relative to H1HA6. Immunization with H1HA10-Foldon also provided significant protection against a higher challenge dose ($2LD_{90}$) of the virus (FIG. 9A).

Example 8

Results (HA Stem Immunogens Confer Robust Subtype-Specific Protection)

Immunogens designed from unmatched, highly drifted influenza strains also elicited a robust immune response in mice with high serum antibody self-titers (≥1,638,400). The ability of stem-immunogens to provide cross-protection was tested against a heightened challenge dose ($2LD_{90}$) of heterologous PR8-virus in mice. All the immunogens significantly delayed viral infection (FIG. 9A, C). NCH1HA10-Foldon conferred robust protection (FIG. 9A), emphasizing the protective ability of stem immunogens across decades of genetic drift. Impressively, the stem fragment NCH1HA10-Foldon designed from a drifted strain (H1N1 A/New Caledonia/20/1999) had greater efficacy relative to the full length stem domain H1HA6 (designed from H1N1 A/PR/8/34) against PR8-virus challenge. H5HA10-Foldon, designed from an H5-subtype influenza strain (H5N1 A/Viet Nam/1203/2004) also provided partial protection and the surviving mice showed significant weight recovery (FIG. 9B). Hence, the protective ability of pH1HA10-Foldon against a Group-2 H3N2 HK68-virus challenge ($2LD_{90}$) was also tested. The immunogen delayed infection and conferred weak protection (FIG. 9C). Surviving mice showed significant weight recovery (FIG. 9D). The 'headless' stem fragment immunogens of the present disclosure confer robust subtype-specific, and weak cross-group protection in vivo.

Overall, these data indicate that the immunogens/polypeptides designed from fragments of HA1, and HA2 stem of influenza virus are surprisingly soluble, correctly folded, and can elicit a robust, broadly cross-reactive, anti-influenza antibody titer in animals, which offer protection from subtype-specific influenza infection in-vivo. Given the homology in the stem, the immunogens/polypeptide of the present disclosure also provides limited hetero-subtypic protection in-vivo. The polypeptides/immunogens as described herein may be used for vaccination against influenza.

It is within the domain of a person ordinarily skilled in the art to develop DNA based vaccines, based on the nucleotide sequences encoding the polypeptides as described herein.

More importantly, the biochemical and biophysical properties of the polypeptides/immunogens as described herein provide support for usage of the polypeptides in various functions, including use as vaccines that are a novel alternative to any attempts made previously. Further, the present disclosure also provides a template for designing of immunogens related to other strains of influenza virus. Lastly, the present disclosure provides a design that can facilitate scale up production of an effective immunogen against a variant of influenza virus in a relatively short period of time that is considerably quicker than current techniques.

SEQUENCES:

SEQ ID NO: 1
DTVDTVLEKNVTVTHSVNLLEDSH.

SEQ ID NO: 2
NSSLPYQNIHPVTIGECPKYVRSAKLRMVTGLRN.

SEQ ID NO: 3
TQNAINGITNKVNTVIEKMNIQFTAVGKEFNKLEKRMENLNKK
VDDGFLDIWTY NAELLVLLENERTLDFHDS.

SEQ ID NO: 4
GACACTGTTGACACAGTACTCGAGAAGAATGTGACAGTGAC
ACACTCTGTTAACCTGCTCGAAGA CAGCCAC.

SEQ ID NO: 5
AACAGCAGTCTCCCTTACCAGAATATACACCCAGTCACAAT
AGGAGAGTGCCCAAAATACGTCAGGAGTGCCAAATTGAGGATGGTTACAG
GACTAAGGAAC.

SEQ ID NO: 6
ACACAAAATGCCATTAACGGGATTACAAACAAGGTGAACAC
TGTTATCGAGAAAATGAACATTCAATTCACAGCTGTGGGTAAAGAATTCA
ACAAATTAGAAAAAAGGATGGAAAATTTAAATAAAAAAGTTGATGATGGA
TTTCTGGACATTTGGACATATAATGCAGAATTGTTAGTTCTACTGGAAAA
TGAAAGGACTCTGGATTTCCATGACTCA.

SEQ ID NO: 7
DTVDTVLEKNVTVTHSVNLLEDSH.

SEQ ID NO: 8
DTVDTVLEKNVTVTHSVNLLEDKH.

SEQ ID NO: 9
EQVDTIMEKNVTVTHAQDILEKTH.

SEQ ID NO: 10
NSSLPYQNTHPTTNGESPKYVRSAKLRMVTGLRN

SEQ ID NO: 11
NSSLPFQNTHPTTNGESPKYVRSAKLRMVTGLRN.

SEQ ID NO: 12
NTSLPFQNTHPTTNGKSPKYVKSTKLRLATGLRN.

SEQ ID NO: 13
NSSMPFHNTHPNTTGESPKYVKSNRLVLATGLRN.

SEQ ID NO: 14
TQNAINGITNKVNTVIEKMNIQDTATGKEFNKDEKRMENLNK
KVDDGFLDIWTYNAELLVLLENERTLDAHDS.

SEQ ID NO: 15
TQNAINGITNKVNSVIEKMNTQDTAVGKEFNKDERRMENLNK
KVDDGFLDIWTYNAELLVLLENERTLDAHDS.

SEQ ID NO: 16
TQNAIDEITNKVNSVIEKMNTQDTAVGKEFNHDEKR1ENLNKK
VDDGFLDIWTYNAELLVLLENERTLDAHDS.

SEQ ID NO: 17
TQKAIDGVTNKVNSIIDKMNTQFEADGREENNDERRIENLNKK
MEDGELDVWTYNAELLVLMENERTLDAHDS.

SEQ ID NO: 18
GATACGGTTGACACGGTCCTGGAAAAGAATGTGACGGTTA
CGCACTC GGTTAATCTGCTGGAAGACTCGCAC.

SEQ ID NO: 19
GACACGGTGGATACGGTCCTGGAAAAGAATGTTACGGTCA
CGCACTCAGTCAATCTGCTGGAAGACAAGCAC.

SEQ ID NO: 20
GAACAAGTGGACACGATTATGGAAAAGAACGTCACGGTTA
CGCACGCCCAAGACATCCTGGAAAAAACGCAC.

SEQ ID NO: 21
AACAGCAGCCTGCCGTATCAGAACACCCATCCGACCACCAA
CGGCGAAAGCCCGAAATATGTGCGTAGCGCGAAACTGCGTATGGTGACCG
GCCTGCGTAAC.

SEQ ID NO: 22
AACTCCTCACTGCCGTTTCAGAACACCCATCCGACCACGAA
TGGTGAAAGTCCGAAATATGTCCGTTCCGCAAAGCTGCGTATGGTTACCG
GTCTGCGTAAT.

SEQ ID NO: 23
AATACGTCACTGCCGTTTCAGAACACCCATCCGACCACGAA
TGGTAAAAGTCCGAAGTATGTTAAATCCACCAAGCTGCGTCTGGCAACCG
GTCTGCGTAAT.

SEQ ID NO: 24
AACAGCTCAATGCCGTTTCATAACACCCACCCGAATACCAC
GGGTGAAAGTCCGAAATATGTCAAGTCCAATCGTCTGGTGCTGGCAACCG
GTCTGCGTAAT.

SEQ ID NO: 25
ACCCAGAACGCGATTAACGGCATTACCAACAAAGTGAACA
CCGTGATTGAAAAAATGAACATTCAGGATACCGCGACCGGCAAAGAATTT
AACAAAGATGAAAAACGTATGGAAAAACCTGAACAAAAAAGTGGATGATGG
CTTTCTGGATATTTGGACCTATAACGCGGAACTGCTGGTGCTGCTGGAAA
ACGAACGTACCCTGGATGCGCATGATAGC.

SEQ ID NO: 26
ACCCAGAACGCAATTAATGGTATCACGAACAAGGTGAACT
CGGTTATCGAAAAGATGAACACCCAAGATACGGCCGTGGGCAAAGAATTT
AATAAGGACGAACGTCGCATGGAAAACCTGAATAAAAAGGTTGATGACGG
TTTCCTGGATATTTGGACCTATAACGCAGAACTGCTGGTCCTGCTGGAAA
ATGAACGTACCCTGGATGCTCACGACTCT.

SEQ ID NO: 27
ACCCAGAATGCAATTGATGAAATCACGAACAAAGTGAATT
CGGTTATTGAAAAGATGAACACCCAAGATACGGCCGTCGGCAAGGAATTC
AACCATGACGAAAGCGTATCGAAAACCTGAACAAGAAGGTCGATGACGG
CTTCCTGGATATCTGGACCTATAACGCAGAACTGCTGGTGCTGCTGGAAA
ATGAACGTACCCTGGATGCTCACGACTCT.

SEQ ID NO: 28
ACCCAGAAAGCAATTGATGGTGTG ACGAACAAGGTTAACT
CGATCATCGATAAGATGAACACCCAATTTGAAGCCGATGGCCGTGAATTC
AACAATGACGAACGTCGCATCGAAAACCTGAATAAAAAGATGGAAGATGG
TTTCCTGGACGTTTGGACCTATAACGCAGAACTGCTGGTCCTGATGGAAA
ATGAACGTACCCTGGATGCTCATGACTCT.

SEQ ID NO: 29
GGCAGCGCGGGCAGCGCG.

SEQ ID NO: 30
GSAGSA.

SEQ ID NO: 31
IKKEIEAIKKEQEAIKKKIEAIEKEIEA

SEQ ID NO: 32
GYIPEAPRDGQAYVRKDGEWVLLSTFL.

SEQ ID NO: 33
ATCAAAAAAGAAATCGAAGCGATCAAAAAAGAACAGGAAG
CCATTAAAAAGAAAATTGAAGCAATCGAAAAAGAAATCGAAGCG.

SEQ ID NO: 34
GGCTATATTCCGGAAGCGCCGCGTGATGGTCAGGCCTACGT
GCGTAAAGATGGCGAATGGGTTCTGCTGAGCACCTTTCTG.

SEQ ID NO: 35
DTVDTVLEKNVTVTHSVNLLEDSHGSANSSLPYQNTHPTTNG
ESPKYVRSAKLRMVTGLRNGSAGSATQNAINGITNKVNTVIEKMNIQDTA
TGKEFNKDEKRMENLNKKVDDGFLDIWTYNAELLVLLENERTLDAHDS.

SEQ ID NO: 36
DTVDTVLEKNVTVTHSVNLLEDSHGSANSSLPYQNTHPTTNG
ESPKYVRSAKLRMVTGLRNGSAGSATQNAINGITNKVNTVIEKMNIQDTA
TGKEFNKDEKRMENLNKKVDDGFLDIWTYNAELLVLLENERTLDAHDSQG
TGGIKKEIEAIKKEQEAIKKKIEAIEKEIEA.

SEQ ID NO: 37
DTVDTVLEKNVTVTHSVNLLEDSHGSANSSLPYQNTHPTTNG
ESPKYVRSAKLRMVTGLRNGSAGSATQNAINGITNKVNTVIEKMNIQDTA
TGKEENKDEKRMENLNKKVDDGELDIWTYNAELLVLLENERTLDAHDSQG
TGGGYIPEAPRDGQAYVRKDGEWVLLSTFL.

SEQ ID NO: 38
DTVDTVLEKNVTVTHSVNLLEDSHGSANSSLPFQNTHPTTNGE
SPKYVRSAKLRMVTGLRNGSAGSATQNAINGITNKVNSVIEKMNTQDTAV
GKEENKDERRMENLNKKVDDGELDIWTYNAELLVLLENERTLDAHDSQGT
GGGYIPEAPRDGQAYVRKDGEWVLLSTFL.

SEQ ID NO: 39
DTVDTVLEKNVTVTHSVNLLEDKHGSANTSLPFQNTHPTTNG
KSPKYVKSTKLRLATGLRNGSAGSATQNAIDEITNKVNSVIEKMNTQDTA
VGKEFNHDEKRIENLNKKVDDGFLDIWTYNAELLVLLENERTLDAHDSQG
TGGGYIPEAPRDGQAYVRKDGEWVLLSTFL.

SEQ ID NO: 40
EQVDTIMEKNVTVTHAQDILEKTHGSANSSMPFHNTHPNTTGE
SPKYVKSNRLVLATGLRNGSAGSATQKAIDGVTNKVNSIIDKMNTQFEAD
GREFNNDERRIENLNKKMEDGFLDVWTYNAELLVLMENERTLDAHDSQGT
GGGYIPEAPRDGQAYVRKDGEWVLLSTFL.

SEQ ID NO: 41
GATACCGTGGATACCGTGCTGGAAAAGAACGTGACCGTGA
CCCATAGCGTGAACCTGCTGGAAGATAGCCATGGCAGCGCGAACAGCAGC
CTGCCGTATCAGAACACCCATCCGACCACCAACGGCGAAAGCCCGAAATA
TGTGCGTAGCGCGAAACTGCGTATGGTGACCGGCCTGCGTAACGGCAGCG
CGGGCAGCGCGACCCAGAACGCGATTAACGGCATTACCAACAAAGTGAAC
ACCGTGATTGAAAAAATGAACATTCAGGATACCGCGACCGGCAAAGAATT
TAACAAAGATGAAAAACGTATGGAAAACCTGAACAAAAAAGTGGATGATG
GCTTTCTGGATATTTGGACCTATAACGCGGAACTGCTGGTGCTGCTGGAA
AACGAACGTACCCTGGATGCGCATGATAGCTAA.

SEQ ID NO: 42:
GATACCGTGGATACCGTGCTGGAAAAGAACGTGACCGTGA
CCCATAGCGTGAACCTGCTGGAAGATAGCCATGGCAGCGCGAACAGCAGC
CTGCCGTATCAGAACACCCATCCGACCACCAACGGCGAAAGCCCGAAATA
TGTGCGTAGCGCGAAACTGCGTATGGTGACCGGCCTGCGTAACGGCAGCG
CGGGCAGCGCGACCCAGAACGCGATTAACGGCATTACCAACAAAGTGAAC
ACCGTGATTGAAAAAATGAACATTCAGGATACCGCGACCGGCAAAGAATT
TAACAAAGATGAAAAACGTATGGAAAACCTGAACAAAAAAGTGGATGATG
GCTTTCTGGATATTTGGACCTATAACGCGGAACTGCTGGTGCTGCTGGAA
AACGAACGTACCCTGGATGCGCATGATAGCCAAGGTACCGGCGGTATCAA
AAAAGAAATCGAAGCGATCAAAAAAGAACAGGAAGCCATTAAAAAGAAAA
TTGAAGCAATCGAAAAAGAAATCGAAGCGTAG.

SEQ ID NO: 43
GATACCGTGGATACCGTGCTGGAAAAGAACGTGACCGTGA
CCCATAGCGTGAACCTGCTGGAAGATAGCCATGGCAGCGCGAACAGCAGC
CTGCCGTATCAGAACACCCATCCGACCACCAACGGCGAAAGCCCGAAATA
TGTGCGTAGCGCGAAACTGCGTATGGTGACCGGCCTGCGTAACGGCAGCG
CGGGCAGCGCGACCCAGAACGCGATTAACGGCATTACCAACAAAGTGAAC
ACCGTGATTGAAAAAATGAACATTCAGGATACCGCGACCGGCAAAGAATT
TAACAAAGATGAAAAACGTATGGAAAACCTGAACAAAAAAGTGGATGATG
GCTTTCTGGATATTTGGACCTATAACGCGGAACTGCTGGTGCTGCTGGAA
AACGAACGTACCCTGGATGCGCATGATAGCCAAGGTACCGGCGGTGGCTA
TATTCCGGAAGCGCCGCGTGATGGTCAGGCCTACGTGCGTAAAGATGGCG
AATGGGTTCTGCTGAGCACCTTTCTGTAA.

SEQ ID NO: 44
GATACGGTTGACACGGTCCTGGAAAAGAATGTGACGGTTA
CGCACTCGGTTAATCTGCTGGAAGACTCGCACGGCTCGGCAAACTCCTCA
CTGCCGTTTCAGAACACCCATCCGACCACGAATGGTGAAAGTCCGAAATA
TGTCCGTTCCGCAAAGCTGCGTATGGTTACCGGTCTGCGTAATGGTAGCG
CCGGCTCTGCAACCCAGAACGCAATTAATGGTATCACGAACAAGGTGAAC
TCGGTTATCGAAAAGATGAACACCCAAGATACGGCCGTGGGCAAAGAATT
TAATAAGGACGAACGTCGCATGGAAAACCTGAATAAAAAGGTTGATGACG
GTTTCCTGGATATTTGGACCTATAACGCAGAACTGCTGGTCCTGCTGGAA
AATGAACGTACCCTGGATGCTCACGACTCTCAAGGCACGGGCGGTGGCTA
CATCCCGGAAGCGCCGCGTGATGGTCAGGCGTATGTTCGTAAAGATGGTG
AATGGGTGCTGCTGTCCACGTTTCTGTGA.

-continued

SEQ ID NO: 45

GACACGGTGGATACGGTCCTGGAAAAGAATGTTACGGTCAC

GCACTCAGTCAATCTGCTGGAAGACAAGCACGGTTCGGCAAATACGTCAC

TGCCGTTTCAGAACACCCATCCGACCACGAATGGTAAAAGTCCGAAGTAT

GTTAAATCCACCAAGCTGCGTCTGGCAACCGGTCTGCGTAATGGTAGCGC

CGGCTCTGCCACCCAGAATGCAATTGATGAAATCACGAACAAAGTGAATT

CGGTTATTGAAAAGATGAACACCCAAGATACGGCCGTCGGCAAGGAATTC

AACCATGACGAAAAGCGTATCGAAAACCTGAACAAGAAGGTCGATGACGG

CTTCCTGGATATCTGGACCTATAACGCAGAACTGCTGGTGCTGCTGGAAA

ATGAACGTACCCTGGATGCTCACGACTCTCAGGGTACGGGCGGTGGCTAC

ATCCCGGAAGCGCCGCGTGATGGTCAGGCGTATGTGCGTAAAGACGGCGA

ATGGGTGCTGCTGTCCACGTTTCTGTGA.

SEQ ID NO: 46

GAACAAGTGGACACGATTATGGAAAAGAACGTCACGGTTA

CGCACGCCCAAGACATCCTGGAAAAAACGCACGGCTCAGCGAACAGCTCA

ATGCCGTTTCATAACACCCACCCGAATACCACGGGTGAAAGTCCGAAATA

TGTCAAGTCCAATCGTCTGGTGCTGGCAACCGGTCTGCGTAATGGTAGCG

CCGGCTCTGCCACCCAGAAAGCAATTGATGGTGTGACGAACAAGGTTAAC

-continued

TCGATCATCGATAAGATGAACACCCAATTTGAAGCCGATGGCCGTGAATT

CAACAATGACGAACGTCGCATCGAAAACCTGAATAAAAAGATGGAAGATG

GTTTCCTGGACGTTTGGACCTATAACGCAGAACTGCTGGTCCTGATGGAA

AATGAACGTACCCTGGATGCTCATGACTCTCAGGGCACGGGCGGTGGCTA

CATTCCGGAAGCGCCGCGTGACGGTCAGGCGTATGTCCGCAAGGATGGTG

AATGGGTGCTGCTGTCCACGTTTCTGTGA.

SEQ ID NO: 47

QGTGG.

SEQ ID NO: 48

CAAGGTACCGGCGGT.

SEQ ID NO: 49

GGGGGG.

SEQ ID NO: 50

GSGSGS.

SEQ ID NO: 51

GSSGSS.

SEQ ID NO: 52

GGCGGCGGTGGTGGCGGC.

SEQ ID NO: 53

GGCTCCGGTTCTGGCTCT.

SEQ ID NO: 54

GGCTCTTCCGGTTCCTCT.

---

We claim:

1. A polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each, subunit is connected by a linker with amino acid sequence selected from the group consisting of GSA, SEQ ID NO: 47, and 30.

2. The polypeptide as claimed in claim 1, wherein each of the second, and third subunit is further modified, wherein the second subunit is modified at amino acid residues selected the group consisting of I9, V12, I14, and C17, and wherein the third subunit is modified at amino acid residues selected from the group consisting of V26, F70, F23, L33, S14, and N42.

3. The polypeptide as claimed in claim 1, wherein the nucleotide sequence encoding the first subunit shares at least 70-100% sequence similarity to a polynucleotide sequence as set forth SEQ ID NO: 4, wherein the nucleotide sequence encoding the second subunit shares at least 70-100% sequence similarity to a polynucleotide sequence as set forth in SEQ ID NO: 5, and wherein the nucleotide sequence encoding the third subunit shares at least 70-100% sequence similarity to, a polynucleotide sequence as set forth in SEQ ID NO: 6.

4. The polypeptide as claimed in claim 1, wherein the amino acid sequence of the first subunit is selected from the group consisting of SEQ ID NO: 7, 8, and 9, wherein the amino acid sequence of the second subunit is selected from the group consisting t f SEQ ID NO: 10, 11, 12, and 13, and wherein the amino acid sequence of the third subunit is selected from the group consisting of SEQ ID NO: 14, 15, 16, and 17.

5. The polypeptide as claimed in claim 4, wherein the nucleotide sequence encoding the first subunit is selected from the group consisting of SEQ ID NO: 18, 19, and 20, wherein the, nucleotide sequence encoding the second subunit is selected from the group consisting of SEQ ID NO: 21, 22, 23, and 24, and wherein the nucleotide sequence encoding the third subunit is selected from the group consisting of SEQ ID NO: 25, 26, 27, and 28.

6. The polypeptide as claimed in claim 1, wherein the nucleotide sequence encoding the linkers is selected from the group consisting of GGCAGCGCG, SEQ ID NO: 48, and 29.

7. The polypeptide as claimed in claim 1, further comprising a C-terminal trimerization motif, wherein said C-terminal trimerization motif amino acid sequence is selected from the group consisting of SEQ ID NO: 31, and 32.

8. The polypeptide as claimed in claim 7, wherein the C-terminal trimerization motif nucleotide sequence is selected from the group consisting of SEQ ID NO: 33, and 34.

9. The polypeptide as claimed in claim 1, wherein the amino acid sequence of the polypeptide is selected from the group consisting of SEQ ID NO: 35, 36, 37, 38, 39, and 40.

10. The polypeptide as claimed in claim 9, wherein the nucleotide sequence encoding the polypeptide is selected from the group consisting of SEQ ID NO: 41, 42, 43, 44, 45, and 46.

11. A recombinant DNA construct comprising a polynucleotide fragment operably linked to a promoter, wherein said polynucleotide fragment encodes a polypeptide comprising a first subunit, a second subunit, and a third subunit, wherein the amino acid sequence of the first subunit shares at least 70-100% sequence similarity to an amino acid sequence as set forth i SEQ ID NO: 1, wherein the amino acid sequence of the second subunit shares at least 70-100% sequence similarity to an amino acid sequence as set forth in SEQ ID NO; 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and 30.

12. A recombinant vector comprising a recombinant DNA construct, said recombinant DNA construct comprising a polynucleotide fragment operably linked to a promoter, wherein said polynucleotide fragment encodes a comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and 30.

13. A recombinant host cell comprising a recombinant vector, said recombinant host cell is selected from the group consisting of a bacterial cell, fungal cell, and mammalian cell, preferably E.coli, wherein said recombinant vector comprises a recombinant DNA construct, said recombinant DNA construct comprising a polynucleotide fragment operably linked to a promoter, wherein said polynucleotide fragment encodes a polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and 30.

14. An influenza vaccine comprising a polypeptide, said polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO; 47, and 30 as claimed in claim 1.

15. A method to produce a vaccine against influenza, said method comprising:
  a. obtaining a host cell comprising a recombinant vector, said recombinant host cell is selected from the group consisting of a bacterial cell, fungal cell, and mammalian cell, preferably E.coli, wherein said recombinant vector comprises a recombinant DNA construct, said recombinant DNA construct comprising a polynucleotide fragment operably linked to a promoter, wherein said polynucleotide fragment encodes a polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO; 2, wherein the amino acid sequence of the third subunit shares at least 70-100% sequence similarity to an amino acid sequence as set forth in SEQ ID NO; 3, and wherein each subunit is connected by a linker with amino acid sequence selected from the group consisting of GSA, SEQ ID NO: 47, and 30
  b. expressing a polypeptide comprising a first subunit, a second subunit, and a third subunit, wherein the amino acid sequence of the first subunit shares, at least 70-100% sequence similarity to an amino acid sequence as set forth in SEQ ID NO: 1, wherein the amino acid sequence of the second subunit shares at least 70-100% sequence similarity to an amino acid sequence as set forth in SEQID No: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO; 47, and 30 from said host cell; and
  c. purifying said polypeptide.

16. An influenza vaccine comprising a polynucleotide fragment encoding a polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and 30.

17. The influenza vaccine as claimed in claim 14 further comprising pharmaceutically acceptable carriers, diluents, and excipients.

18. A polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and for use as a vaccine against influenza.

19. A method of administering a vaccine to a subject in need of creating an immune response against influenza in said subject cell tissue, said method comprising;
   a. obtaining a prophylactically effective amount of an influenza vaccine comprising a polynucleotide fragment encoding a polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and; or a polypeptide comprising a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and; and
   b. administering said effective amount of influenza vaccine or polypeptide to said subject, wherein said method creates an immune response against influenza.

20. The method as claimed in claim 19, wherein said administration is oral, intramuscular, or intraperitoneal.

21. An influenza vaccine comprising a polypeptide, said polypeptide a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ NO: 47, and 30 as claimed in claim 2.

22. An influenza vaccine comprising a polypeptide, said polypeptide a first subunit, a second subunit, and a third subunit, wherein the amino acid sequence of the first subunit shares at least 70-100% sequence similarity to an amino acid sequence as set forth in. SEQ ID NO: 1, wherein the amino acid sequence of the second subunit shares at least 70-100% sequence similarity to an amino acid sequence as set forth M SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and 30 as hued in claim 5.

23. An influenza vaccine comprising a polypeptide, said polypeptide a first subunit, a second subunit, and ,a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-100% sequence similarity to an amino acid sequence as set forth in SEQ ID NO: 3, and wherein each subunit is connected by a linker with amino acid sequence selected from the group consisting of GSA, SEQ ID NO: 47, and 30 as claimed in claim 8.

24. An influenza vaccine comprising a polypeptide, said polypeptide a first subunit, a second subunit, and a third subunit, wherein the amino acid sequence of the first subunit shares at least 70-100% sequence similarity to an amino acid sequence as set forth in SEQ ID NO: 1, wherein the amino acid sequence of the second subunit shares at least 70-100% sequence similarity to an amino acid sequence as set forth in SEQ ID NO: 2, wherein the amino acid sequence of the third subunit shares at least 70-400% sequence similarity to an amino acid sequence as set forth in SEQ ID NO: 3, and wherein each subunit is connected by a linker with amino acid sequence selected from the group consisting of GSA, SEQ ID NO: 47, and 30 as claimed in claim 10.

\* \* \* \* \*

SEQUENCE LISTING

<160> NUMBER OF SEQ ID NOS: 54

<210> SEQ ID NO 1
<211> LENGTH: 24
<212> TYPE: PRT
<213> ORGANISM: artificial sequence
<220> FEATURE:
<223> OTHER INFORMATION: HA1 fragment first subunit of polypeptide

<400> SEQUENCE: 1

```
Asp Thr Val Asp Thr Val Leu Glu Lys Asn Val Thr Val Thr His Ser
1               5                   10                  15

Val Asn Leu Leu Glu Asp Ser His
            20
```

<210> SEQ ID NO 2
<211> LENGTH: 34
<212> TYPE: PRT
<213> ORGANISM: artificial sequence
<220> FEATURE:
<223> OTHER INFORMATION: HA1 fragment second subunit of polypeptide

<400> SEQUENCE: 2

```
Asn Ser Ser Leu Pro Tyr Gln Asn Ile His Pro Val Thr Ile Gly Glu
1               5                   10                  15

Cys Pro Lys Tyr Val Arg Ser Ala Lys Leu Arg Met Val Thr Gly Leu
            20                  25                  30

Arg Asn
```

<210> SEQ ID NO 3
<211> LENGTH: 73
<212> TYPE: PRT

<213> ORGANISM: artificial sequence
<220> FEATURE:
<223> OTHER INFORMATION: HA2 fragment third subunit of polypeptide

<400> SEQUENCE: 3

```
Thr Gln Asn Ala Ile Asn Gly Ile Thr Asn Lys Val Asn Thr Val Ile
1               5                   10                  15

Glu Lys Met Asn Ile Gln Phe Thr Ala Val Gly Lys Glu Phe Asn Lys
            20                  25                  30

Leu Glu Lys Arg Met Glu Asn Leu Asn Lys Lys Val Asp Asp Gly Phe
        35                  40                  45

Leu Asp Ile Trp Thr Tyr Asn Ala Glu Leu Leu Val Leu Leu Glu Asn
    50                  55                  60

Glu Arg Thr Leu Asp Phe His Asp Ser
65                  70
```

<210> SEQ ID NO 4
<211> LENGTH: 72
<212> TYPE: DNA
<213> ORGANISM: artificial sequence
<220> FEATURE:
<223> OTHER INFORMATION: HA1 fragment first subunit of polypeptide

<400> SEQUENCE: 4

```
gacactgttg acacagtact cgagaagaat gtgacagtga cacactctgt taacctgctc     60
gaagacagcc ac                                                         72
```

<210> SEQ ID NO 5
<211> LENGTH: 102
<212> TYPE: DNA
<213> ORGANISM: artificial sequence
<220> FEATURE:
<223> OTHER INFORMATION: HA1 fragment second subunit of polypeptide

<400> SEQUENCE: 5

```
aacagcagtc tcccttacca gaatatacac ccagtcacaa taggagagtg cccaaaatac     60
gtcaggagtg ccaaattgag gatggttaca ggactaagga ac                       102
```

<210> SEQ ID NO 6
<211> LENGTH: 219
<212> TYPE: DNA
<213> ORGANISM: artificial sequence
<220> FEATURE:
<223> OTHER INFORMATION: HA2 fragment third subunit of polypeptide

<400> SEQUENCE: 6

```
acacaaaatg ccattaacgg gattacaaac aaggtgaaca ctgttatcga gaaaatgaac     60
attcaattca cagctgtggg taaagaattc aacaaattag aaaaaaggat ggaaaattta    120
aataaaaaag ttgatgatgg atttctggac atttggacat ataatgcaga attgttagtt    180
ctactggaaa atgaaaggac tctggatttc catgactca                           219
```

<210> SEQ ID NO 7
<211> LENGTH: 24
<212> TYPE: PRT
<213> ORGANISM: artificial sequence
<220> FEATURE:
<223> OTHER INFORMATION: HA1 fragment of H1N1 A/New Caledonia/20/99HA1
      first subunit of polypeptide

<400> SEQUENCE: 7

```
Asp Thr Val Asp Thr Val Leu Glu Lys Asn Val Thr Val Thr His Ser
```

```
Val Asn Leu Leu Glu Asp Ser His
            20

<210> SEQ ID NO 8
<211> LENGTH: 24
<212> TYPE: PRT
<213> ORGANISM: artificial sequence
<220> FEATURE:
<223> OTHER INFORMATION: HA1 fragment of H1N1 A/California/04/2009 first

```
<211> LENGTH: 34
<212> TYPE: PRT
<213> ORGANISM: artificial sequence
<220> FEATURE:
<223> OTHER INFORMATION: HA1 fragment of H1NI Asp Glu Arg Arg Met Glu Asn Leu Asn Lys Lys Val Asp Gly Phe
             35                  40                  45

Leu Asp Ile Trp Thr Tyr Asn Ala Glu Leu Leu Val Leu Leu Glu Asn
     50                  55                  60

Glu Arg Thr Leu Asp Ala His Asp Ser
65                  70

<210> SEQ ID NO 16
<211> LENGTH: 73
<212> TYPE: PRT
<213> ORGANISM: artificial sequence
<220> FEATURE:
<223> OTHER INFORMATION: HA2 fragment of H1N1 A/California/04/2009 third
      subunit of polypeptide

<400> SEQUENCE: 16

Thr Gln Asn Ala Ile Asp Glu Ile Thr Asn Lys Val Asn Ser Val Ile
1               5                   10                  15

Glu Lys Met Asn Thr Gln Asp Thr Ala Val Gly Lys Glu Phe Asn His
             20                  25                  30

Asp Glu Lys Arg Ile Glu Asn Leu Asn Lys Lys Val Asp Asp Gly Phe
             35                  40                  45

Leu Asp Ile Trp Thr Tyr Asn Ala Glu Leu Leu Val Leu Leu Glu Asn
     50                  55                  60

Glu Arg Thr Leu Asp Ala His Asp Ser
65                  70

<210> SEQ ID NO 17
<211> LENGTH: 73
<212> TYPE: PRT
<213> ORGANISM: artificial sequence
<220> FEATURE:
<223> OTHER INFORMATION: HA2 fragment of H5N1 A/Viet Nam/1203/2004 third
      subunit of polypeptide

<400> SEQUENCE: 17

Thr Gln Lys Ala Ile Asp Gly Val Thr Asn Lys Val Asn Ser Ile Ile
1               5                   10                  15

Asp Lys Met Asn Thr Gln Phe Glu Ala Asp Gly Arg Glu Phe Asn Asn
             20                  25                  30

Asp Glu Arg Arg Ile Glu Asn Leu Asn Lys Lys Met Glu Asp Gly Phe
             35                  40                  45

Leu Asp Val Trp Thr Tyr Asn Ala Glu Leu Leu Val Leu Met Glu Asn
     50                  55                  60

Glu Arg Thr Leu Asp Ala His Asp Ser
65                  70

<210> SEQ ID NO 18
<211> LENGTH: 72
<212> TYPE: DNA
<213> ORGANISM: artificial sequence
<220> FEATURE:
<223> OTHER INFORMATION: DNA sequence of SEQ ID NO: 7

<400> SEQUENCE: 18
gatacggttg acacggtcct ggaaaagaat gtgacggtta cgcactcggt taatctgctg     60
gaagactcgc ac                                                        72

<210> SEQ ID NO 19
<211> LENGTH: 72
<212> TYPE: DNA

<213> ORGANISM: artificial sequence
<220> FEATURE:
<223> OTHER INFORMATION: DNA sequnce of SEQ ID NO: 8

<400> SEQUENCE: 19
gacacggtgg atacggtcct ggaaaagaat gttacggtca cgcactcagt caatctgctg    60
gaagacaagc ac                                                       72

<210> SEQ ID NO 20
<211> LENGTH: 72
<212> TYPE: DNA
<213> ORGANISM: artificial sequence
<220> FEATURE:
<223> OTHER INFORMATION: DNA sequence of SEQ ID NO: 9

<400> SEQUENCE: 20
gaacaagtgg acacgattat ggaaaagaac gtcacggtta cgcacgccca agacatcctg    60
gaaaaaacgc ac                                                       72

<210> SEQ ID NO 21
<211> LENGTH: 102
<212> TYPE: DNA
<213> ORGANISM: artificial sequence
<220> FEATURE:
<223> OTHER INFORMATION: DNA sequence of SEQ ID NO: 10

<400> SEQUENCE: 21
aacagcagcc tgccgtatca gaacacccat ccgaccacca acggcgaaag cccgaaatat    60
gtgcgtagcg cgaaactgcg tatggtgacc ggcctgcgta ac                     102

<210> SEQ ID NO 22
<211> LENGTH: 102
<212> TYPE: DNA
<213> ORGANISM: artificial sequence
<220> FEATURE:
<223> OTHER INFORMATION: DNA sequence of SEQ ID NO: 11

<400> SEQUENCE: 22
aactcctcac tgccgtttca gaacacccat ccgaccacga atggtgaaag tccgaaatat    60
gtccgttccg caaagctgcg tatggttacc ggtctgcgta at                     102

<210> SEQ ID NO 23
<211> LENGTH: 102
<212> TYPE: DNA
<213> ORGANISM: artificial sequence
<220> FEATURE:
<223> OTHER INFORMATION: DNA sequence of SEQ ID NO: 12

<400> SEQUENCE: 23
aatacgtcac tgccgtttca gaacacccat ccgaccacga atggtaaaag tccgaagtat    60
gttaaatcca ccaagctgcg tctggcaacc ggtctgcgta at                     102

<210> SEQ ID NO 24
<211> LENGTH: 102
<212> TYPE: DNA
<213> ORGANISM: artificial sequence
<220> FEATURE:
<223> OTHER INFORMATION: DNA sequence of SEQ ID NO: 13

<400> SEQUENCE: 24
aacagctcaa tgccgtttca taacacccac ccgaatacca cgggtgaaag tccgaaatat    60
gtcaagtcca atcgtctggt gctggcaacc ggtctgcgta at                     102

```
<210> SEQ ID NO 25
<211> LENGTH: 219
<212> TYPE: DNA
<213> ORGANISM: artificial sequence
<220> FEATURE:
<223> OTHER INFORMATION: DNA sequence of SEQ ID NO: 14

<400> SEQUENCE: 25
acccagaacg cgattaacgg cattaccaac aaagtgaaca ccgtgattga aaaaatgaac      60
attcaggata ccgcgaccgg caaagaattt aacaaagatg aaaaacgtat ggaaaacctg     120
aacaaaaaag tggatgatgg ctttctggat atttggacct ataacgcgga actgctggtg     180
ctgctggaaa acgaacgtac cctggatgcg catgatagc                            219

<210> SEQ ID NO 26
<211> LENGTH: 219
<212> TYPE: DNA
<213> ORGANISM: artificial sequence
<220> FEATURE:
<223> OTHER INFORMATION: DNA sequence of SEQ ID NO: 15

<400> SEQUENCE: 26
acccagaacg caattaatgg tatcacgaac aaggtgaact cggttatcga aaagatgaac      60
acccaagata cggccgtggg caaagaattt aataaggacg aacgtcgcat ggaaaacctg     120
aataaaaagg ttgatgacgg tttcctggat atttggacct ataacgcaga actgctggtc     180
ctgctggaaa atgaacgtac cctggatgct cacgactct                            219

<210> SEQ ID NO 27
<211> LENGTH: 219
<212> TYPE: DNA
<213> ORGANISM: artificial sequence
<220> FEATURE:
<223> OTHER INFORMATION: DNA sequence of SEQ ID NO: 16

<400> SEQUENCE: 27
acccagaatg caattgatga aatcacgaac aaagtgaatt cggttattga aaagatgaac      60
acccaagata cggccgtcgg caaggaattc aaccatgacg aaaagcgtat cgaaaacctg     120
aacaagaagg tcgatgacgg cttcctggat atctggacct ataacgcaga actgctggtg     180
ctgctggaaa atgaacgtac cctggatgct cacgactct                            219

<210> SEQ ID NO 28
<211> LENGTH: 219
<212> TYPE: DNA
<213> ORGANISM: artificial sequence
<220> FEATURE:
<223> OTHER INFORMATION: DNA sequence of SEQ ID NO: 17

<400> SEQUENCE: 28
acccagaaag caattgatgg tgtgacgaac aaggttaact cgatcatcga taagatgaac      60
acccaatttg aagccgatgg ccgtgaattc aacaatgacg aacgtcgcat cgaaaacctg     120
aataaaaaga tggaagatgg tttcctggac gtttggacct ataacgcaga actgctggtc     180
ctgatggaaa atgaacgtac cctggatgct catgactct                            219

<210> SEQ ID NO 29
<211> LENGTH: 18
<212> TYPE: DNA
<213> ORGANISM: artificial sequence
<220> FEATURE:
```

<223> OTHER INFORMATION: DNA sequence of SEQ ID NO: 30

<400> SEQUENCE: 29
ggcagcgcgg gcagcgcg                                                18

<210> SEQ ID NO 30
<211> LENGTH: 6
<212> TYPE: PRT
<213> ORGANISM: artificial sequence
<220> FEATURE:
<223> OTHER INFORMATION: linker sequence

<400> SEQUENCE: 30

Gly Ser Ala Gly Ser Ala
1               5

<210> SEQ ID NO 31
<211> LENGTH: 28
<212> TYPE: PRT
<213> ORGANISM: artificial sequence
<220> FEATURE:
<223> OTHER INFORMATION: isoleucine zipper trimerization motif

<400> SEQUENCE: 31

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Ala
            20                  25

<210> SEQ ID NO 32
<211> LENGTH: 27
<212> TYPE: PRT
<213> ORGANISM: artificial sequence
<220> FEATURE:
<223> OTHER INFORMATION: Foldon sequence trimerization motif

<400> SEQUENCE: 32

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 33
<211> LENGTH: 84
<212> TYPE: DNA
<213> ORGANISM: artificial sequence
<220> FEATURE:
<223> OTHER INFORMATION: DNA sequence of SEQ ID NO: 31

<400> SEQUENCE: 33
atcaaaaaag aaatcgaagc gatcaaaaaa gaacaggaag ccattaaaaa gaaaattgaa     60
gcaatcgaaa aagaaatcga agcg                                           84

<210> SEQ ID NO 34
<211> LENGTH: 81
<212> TYPE: DNA
<213> ORGANISM: artificial sequence
<220> FEATURE:
<223> OTHER INFORMATION: DNA sequence of SEQ ID NO: 32

<400> SEQUENCE: 34
ggctatattc cggaagcgcc gcgtgatggt caggcctacg tgcgtaaaga tggcgaatgg     60
gttctgctga gcacctttct g                                              81

<210> SEQ ID NO 35
<211> LENGTH: 140
<212> TYPE: PRT
<213> ORGANISM: artificial sequence
<220> FEATURE:
<223> OTHER INFORMATION: sequence of H1HA10 (H1N1 A/Puerto Rico/8/34)
      polypeptide

<400> SEQUENCE: 35

Asp Thr Val Asp Thr Val Le

<210> SEQ ID NO 37
<211> LENGTH: 172
<212> TYPE: PRT
<213> ORGANISM: artificial sequence
<220> FEATURE:
<223> OTHER INFORMATION: sequence of H1HA10-Foldon(H1N1 A/Puerto Rico/8/34)

<400> SEQUENCE: 37

Asp Thr Val Asp Thr Val Leu Glu Lys Asn Val Thr Val Thr His Ser
1 5 10 15

Val Asn Leu Leu Glu Asp Ser His Gly Ser Ala Asn Ser Ser Leu Pro
20 25 30

Tyr Gln Asn Thr His Pro Thr Thr Asn Gly Glu Ser Pro Lys Tyr Val
35 40 45

Arg Ser Ala Lys Leu Arg Met Val Thr Gly Leu Arg Asn Gly Ser Ala
50 55 60

Gly Ser Ala Thr Gln Asn Ala Ile Asn Gly Ile Thr Asn Lys Val Asn
65 70 75 80

Thr Val Ile Glu Lys Met Asn Ile Gln Asp Thr Ala Thr Gly Lys Glu
85 90 95

Phe Asn Lys Asp Glu Lys Arg Met Glu Asn Leu Asn Lys Lys Val Asp
100 105 110

Asp Gly Phe Leu Asp Ile Trp Thr Tyr Asn Ala Glu Leu Leu Val Leu
115 120 125

Leu Glu Asn Glu Arg Thr Leu Asp Ala His Asp Ser Gln Gly Thr Gly
130 135 140

Gly Gly Tyr Ile Pro Glu Ala Pro Arg Asp Gly Gln Ala Tyr Val Arg
145 150 155 160

Lys Asp Gly Glu Trp Val Leu Leu Ser Thr Phe Leu
165 170

<210> SEQ ID NO 38
<211> LENGTH: 172
<212> TYPE: PRT
<213> ORGANISM: artificial sequence
<220> FEATURE:
<223> OTHER INFORMATION: sequence of NCH1HA1-Foldon (H1NI A/New Caledonia/20/99)

<400> SEQUENCE: 38

Asp Thr Val Asp Thr Val Leu Glu Lys Asn Val Thr Val Thr His Ser
1 5 10 15

Val Asn Leu Leu Glu Asp Ser His Gly Ser Ala Asn Ser Ser Leu Pro
20 25 30

Phe Gln Asn Thr His Pro Thr Thr Asn Gly Glu Ser Pro Lys Tyr Val
35 40 45

Arg Ser Ala Lys Leu Arg Met Val Thr Gly Leu Arg Asn Gly Ser Ala
50 55 60

Gly Ser Ala Thr Gln Asn Ala Ile Asn Gly Ile Thr Asn Lys Val Asn
65 70 75 80

Ser Val Ile Glu Lys Met Asn Thr Gln Asp Thr Ala Val Gly Lys Glu
85 90 95

Phe Asn Lys Asp Glu Arg Arg Met Glu Asn Leu Asn Lys Lys Val Asp
100 105 110

Asp Gly Phe Leu Asp Ile Trp Thr Tyr Asn Ala Glu Leu Leu Val Leu

```
                        115                 120                 125

Leu Glu Asn Glu Arg Thr Leu Asp Ala His Asp Ser Gln Gly Thr Gly
            130                 135                 140

Gly Gly Tyr Ile Pro Glu Ala Pro Arg Asp Gly Gln Ala Tyr Val Arg
145                 150                 155                 160

Lys Asp Gly Glu Trp Val Leu Leu Ser Thr Phe Leu
                165                 170

<210> SEQ ID NO 39
<211> LENGTH: 172
<212> TYPE: PRT
<213> ORGANISM: artificial sequence
<220> FEATURE:
<223> OTHER INFORMATION: sequence of pH1HA1-Foldon (H1N1
      A/California/04/2009)

<400> SEQUENCE: 39

Asp Thr Val Asp Thr Val Leu Glu Lys Asn Val Thr Val Thr His Ser
1               5                   10                  15

Val Asn Leu Leu Glu Asp Lys His Gly Ser Ala Asn Thr Ser Leu Pro
            20                  25                  30

Phe Gln Asn Thr His Pro Thr Thr Asn Gly Lys Ser Pro Lys Tyr Val
        35                  40                  45

Lys Ser Thr Lys Leu Arg Leu Ala Thr Gly Leu Arg Asn Gly Ser Ala
    50                  55                  60

Gly Ser Ala Thr Gln Asn Ala Ile Asp Glu Ile Thr Asn Lys Val Asn
65                  70                  75                  80

Ser Val Ile Glu Lys Met Asn Thr Gln Asp Thr Ala Val Gly Lys Glu
                85                  90                  95

Phe Asn His Asp Glu Lys Arg Ile Glu Asn Leu Asn Lys Lys Val Asp
            100                 105                 110

Asp Gly Phe Leu Asp Ile Trp Thr Tyr Asn Ala Glu Leu Leu Val Leu
        115                 120                 125

Leu Glu Asn Glu Arg Thr Leu Asp Ala His Asp Ser Gln Gly Thr Gly
            130                 135                 140

Gly Gly Tyr Ile Pro Glu Ala Pro Arg Asp Gly Gln Ala Tyr Val Arg
145                 150                 155                 160

Lys Asp Gly Glu Trp Val Leu Leu Ser Thr Phe Leu
                165                 170

<210> SEQ ID NO 40
<211> LENGTH: 172
<212> TYPE: PRT
<213> ORGANISM: artificial sequence
<220> FEATURE:
<223> OTHER INFORMATION: sequence of H5HA10-Foldon (H5N1 A/Viet
      Nam/1203/2004)

<400> SEQUENCE: 40

Glu Gln Val Asp Thr Ile Met Glu Lys Asn Val Thr Val Thr His Ala
1               5                   10                  15

Gln Asp Ile Leu Glu Lys Thr His Gly Ser Ala Asn Ser Ser Met Pro
            20                  25                  30

Phe His Asn Thr His Pro Asn Thr Thr Gly Glu Ser Pro Lys Tyr Val
        35                  40                  45

Lys Ser Asn Arg Leu Val Leu Ala Thr Gly Leu Arg Asn Gly Ser Ala
    50                  55                  60

Gly Ser Ala Thr Gln Lys Ala Ile Asp Gly Val Thr Asn Lys Val Asn
```

```
                65                  70                  75                  80
Ser Ile Ile Asp Lys Met Asn Thr Gln Phe Glu Ala Asp Gly Arg Glu
                    85                  90                  95

Phe Asn Asn Asp Glu Arg Arg Ile Glu Asn Leu Asn Lys Lys Met Glu
                    100                 105                 110

Asp Gly Phe Leu Asp Val Trp Thr Tyr Asn Ala Glu Leu Leu Val Leu
                    115                 120                 125

Met Glu Asn Glu Arg Thr Leu Asp Ala His Asp Ser Gln Gly Thr Gly
                    130                 135                 140

Gly Gly Tyr Ile Pro Glu Ala Pro Arg Asp Gly Gln Ala Tyr Val Arg
145                 150                 155                 160

Lys Asp Gly Glu Trp Val Leu Leu Ser Thr Phe Leu
                    165                 170

<210> SEQ ID NO 41
<211> LENGTH: 423
<212> TYPE: DNA
<213> ORGANISM: artificial sequence
<220> FEATURE:
<223> OTHER INFORMATION: DNA sequence of SEQ ID NO: 35

<400> SEQUENCE: 41
gataccgtgg ataccgtgct ggaaaagaac gtgaccgtga cccatagcgt gaacctgctg      60
gaagatagcc atggcagcgc gaacagcagc ctgccgtatc agaacaccca tccgaccacc     120
aacggcgaaa gcccgaaata tgtgcgtagc gcgaaactgc gtatggtgac cggcctgcgt     180
aacggcagcg cgggcagcgc gacccagaac gcgattaacg cgattaccaa caaagtgaac     240
accgtgattg aaaaaatgaa cattcaggat accgcgaccg gcaaagaatt taacaaagat     300
gaaaaacgta tggaaaacct gaacaaaaaa gtggatgatg ctttctggaa tatttggacc     360
tataacgcgg aactgctggt gctgctggaa acgaacgta ccctggatgc gcatgatagc      420
taa                                                                   423

<210> SEQ ID NO 42
<211> LENGTH: 522
<212> TYPE: DNA
<213> ORGANISM: artificial sequence
<220> FEATURE:
<223> OTHER INFORMATION: DNA sequenece of SEQ ID NO: 36

<400> SEQUENCE: 42
gataccgtgg ataccgtgct ggaaaagaac gtgaccgtga cccatagcgt gaacctgctg      60
gaagatagcc atggcagcgc gaacagcagc ctgccgtatc agaacaccca tccgaccacc     120
aacggcgaaa gcccgaaata tgtgcgtagc gcgaaactgc gtatggtgac cggcctgcgt     180
aacggcagcg cgggcagcgc gacccagaac gcgattaacg cgattaccaa caaagtgaac     240
accgtgattg aaaaaatgaa cattcaggat accgcgaccg gcaaagaatt taacaaagat     300
gaaaaacgta tggaaaacct gaacaaaaaa gtggatgatg ctttctggaa tatttggacc     360
tataacgcgg aactgctggt gctgctggaa acgaacgta ccctggatgc gcatgatagc      420
caaggtaccg gcggtatcaa aaaagaaatc gaagcgatca aaaaagaaca ggaagccatt     480
aaaaagaaaa ttgaagcaat cgaaaagaa atcgaagcgt ag                         522

<210> SEQ ID NO 43
<211> LENGTH: 519
<212> TYPE: DNA
<213> ORGANISM: artificial sequence
```

<220> FEATURE:
<223> OTHER INFORMATION: DNA sequence of SEQ ID NO: 37

<400> SEQUENCE: 43

```
gataccgtgg ataccgtgct ggaaaagaac gtgaccgtga cccatagcgt gaacctgctg    60
gaagatagcc atggcagcgc gaacagcagc ctgccgtatc agaacaccca tccgaccacc   120
aacggcgaaa gcccgaaata tgtgcgtagc gcgaaactgc gtatggtgac cggcctgcgt   180
aacggcagcg cgggcagcgc gacccagaac gcgattaacg gcattaccaa caaagtgaac   240
accgtgattg aaaaaatgaa cattcaggat accgcgaccg gcaaagaatt aacaaagat   300
gaaaaacgta tggaaaacct gaacaaaaaa gtggatgatg ctttctgga tatttggacc   360
tataacgcgg aactgctggt gctgctggaa aacgaacgta ccctggatgc gcatgatagc   420
caaggtaccg gcggtggcta tattccggaa gcgccgcgtg atggtcaggc ctacgtgcgt   480
aaagatggcg aatgggttct gctgagcacc tttctgtaa                         519
```

<210> SEQ ID NO 44
<211> LENGTH: 519
<212> TYPE: DNA
<213> ORGANISM: artificial sequence
<220> FEATURE:
<223> OTHER INFORMATION: DNA sequence of SEQ ID NO: 38

<400> SEQUENCE: 44

```
gatacggttg acacggtcct ggaaaagaat gtgacggtta cgcactcggt taatctgctg    60
gaagactcgc acggctcggc aaactcctca ctgccgtttc agaacaccca tccgaccacg   120
aatggtgaaa gtccgaaata tgtccgttcc gcaaagctgc gtatggttac cggtctgcgt   180
aatggtagcg ccggctctgc aacccagaac gcaattaatg gtatcacgaa caaggtgaac   240
tcggttatcg aaaagatgaa cacccaagat acggccgtgg gcaaagaatt aataaggac   300
gaacgtcgca tggaaaacct gaataaaaag gttgatgacg gtttcctgga tatttggacc   360
tataacgcag aactgctggt cctgctggaa aatgaacgta ccctggatgc tcacgactct   420
caaggcacgg gcggtggcta catcccggaa gcgccgcgtg atggtcaggc gtatgttcgt   480
aaagatggtg aatgggtgct gctgtccacg tttctgtga                         519
```

<210> SEQ ID NO 45
<211> LENGTH: 519
<212> TYPE: DNA
<213> ORGANISM: artificial sequence
<220> FEATURE:
<223> OTHER INFORMATION: DNA sequence of SEQ ID NO: 39

<400> SEQUENCE: 45

```
gacacggtgg atacggtcct ggaaaagaat gttacggtca cgcactcagt caatctgctg    60
gaagacaagc acggttcggc aaatacgtca ctgccgtttc agaacaccca tccgaccacg   120
aatggtaaaa gtccgaagta tgttaaatcc accaagctgc gtctggcaac cggtctgcgt   180
aatggtagcg ccggctctgc cacccagaat gcaattgatg aaatcacgaa caaagtgaat   240
tcggttattg aaaagatgaa cacccaagat acggccgtcg gcaaggaatt caaccatgac   300
gaaaagcgta tcgaaaacct gaacaagaag gtcgatgacg gcttcctgga tatctggacc   360
tataacgcag aactgctggt gctgctggaa aatgaacgta ccctggatgc tcacgactct   420
cagggtacgg gcggtggcta catcccggaa gcgccgcgtg atggtcaggc gtatgtgcgt   480
aaagacggcg aatgggtgct gctgtccacg tttctgtga                         519
```

<210> SEQ ID NO 46
<211> LENGTH: 519
<212> TYPE: DNA
<213> ORGANISM: artificial sequence
<220> FEATURE:
<223> OTHER INFORMATION: DNA sequence of SEQ ID NO: 40

<400> SEQUENCE: 46

```
gaacaagtgg acacgattat ggaaaagaac gtcacggtta cgcacgccca agacatcctg      60
gaaaaacgc acggctcagc gaacagctca atgccgtttc ataacaccca cccgaatacc     120
acgggtgaaa gtccgaaata tgtcaagtcc aatcgtctgg tgctggcaac cggtctgcgt    180
aatggtagcg ccggctctgc cacccagaaa gcaattgatg gtgtgacgaa caaggttaac    240
tcgatcatcg ataagatgaa cacccaattt gaagccgatg ccgtgaatt caacaatgac     300
gaacgtcgca tcgaaaacct gaataaaaag atggaagatg gtttcctgga cgtttggacc    360
tataacgcag aactgctggt cctgatggaa atgaacgta ccctggatgc tcatgactct     420
cagggcacgg gcggtggcta cattccggaa gcgccgcgtg acggtcaggc gtatgtccgc    480
aaggatggtg aatgggtgct gctgtccacg tttctgtga                           519
```

<210> SEQ ID NO 47
<211> LENGTH: 5
<212> TYPE: PRT
<213> ORGANISM: artificial sequence
<220> FEATURE:
<223> OTHER INFORMATION: linker sequence

<400> SEQUENCE: 47

Gln Gly Thr Gly Gly
1               5

<210> SEQ ID NO 48
<211> LENGTH: 15
<212> TYPE: DNA
<213> ORGANISM: artificial sequence
<220> FEATURE:
<223> OTHER INFORMATION: DNA sequence of SEQ ID NO: 47

<400> SEQUENCE: 48
caaggtaccg gcggt                                                      15

<210> SEQ ID NO 49
<211> LENGTH: 6
<212> TYPE: PRT
<213> ORGANISM: artificial sequence
<220> FEATURE:
<223> OTHER INFORMATION: linker sequence

<400> SEQUENCE: 49

Gly Gly Gly Gly Gly Gly
1               5

<210> SEQ ID NO 50
<211> LENGTH: 6
<212> TYPE: PRT
<213> ORGANISM: artificial sequence
<220> FEATURE:
<223> OTHER INFORMATION: linker sequence

<400> SEQUENCE: 50

Gly Ser Gly Ser Gly Ser
1               5

```
<210> SEQ ID NO 51
<211> LENGTH: 6
<212> TYPE: PRT
<213> ORGANISM: artificial sequence
<220> FEATURE:
<223> OTHER INFORMATION: linker sequence

<400> SEQUENCE: 51

Gly Ser Ser Gly Ser Ser
1               5

<210> SEQ ID NO 52
<211> LENGTH: 18
<212> TYPE: DNA
<213> ORGANISM: artificial sequence
<220> FEATURE:
<223> OTHER INFORMATION: DNA sequence of SEQ ID NO: 49

<400> SEQUENCE: 52
ggcggcggtg gtggcggc                                                 18

<210> SEQ ID NO 53
<211> LENGTH: 18
<212> TYPE: DNA
<213> ORGANISM: artificial sequence
<220> FEATURE:
<223> OTHER INFORMATION: DNA sequence of SEQ ID NO: 50

<400> SEQUENCE: 53
ggctccggtt ctggctct                                                 18

<210> SEQ ID NO 54
<211> LENGTH: 18
<212> TYPE: DNA
<213> ORGANISM: artificial sequence
<220> FEATURE:
<223> OTHER INFORMATION: DNA sequence of SEQ ID NO: 51

<400> SEQUENCE: 54
ggctcttccg gttcctct                                                 18
```